United States Patent
Hirose et al.

(10) Patent No.: US 10,451,861 B2
(45) Date of Patent: Oct. 22, 2019

(54) MEDICAL OBSERVATION DEVICE AND MEDICAL OBSERVATION SYSTEM

(71) Applicant: Sony Olympus Medical Solutions Inc., Tokyo (JP)

(72) Inventors: Kenji Hirose, Tokyo (JP); Gakuji Higuchi, Tokyo (JP); Yasuhiro Okabe, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 86 days.

(21) Appl. No.: 15/702,782

(22) Filed: Sep. 13, 2017

(65) Prior Publication Data

US 2018/0081160 A1    Mar. 22, 2018

(30) Foreign Application Priority Data

Sep. 21, 2016  (JP) ................. 2016-183964

(51) Int. Cl.
| | | |
|---|---|---|
| *G02B 21/24* | (2006.01) | |
| *G02B 21/00* | (2006.01) | |
| *A61B 90/25* | (2016.01) | |
| *G02B 21/36* | (2006.01) | |

(52) U.S. Cl.
CPC ............. *G02B 21/24* (2013.01); *A61B 90/25* (2016.02); *G02B 21/0012* (2013.01); *G02B 21/36* (2013.01); *G02B 21/368* (2013.01)

(58) Field of Classification Search
CPC .... G02B 21/24; G02B 21/0012; G02B 21/36; G02B 21/368; A61B 90/25
USPC ...................................... 359/384
See application file for complete search history.

(56) References Cited

U.S. PATENT DOCUMENTS

| | | | | |
|---|---|---|---|---|
| 5,122,904 A * | 6/1992 | Fujiwara | ............... | A61B 90/25 359/510 |
| 6,398,721 B1 * | 6/2002 | Nakamura | ............ | G02B 7/001 359/385 |
| 6,661,571 B1 * | 12/2003 | Shioda | .................... | A61B 1/04 359/368 |
| 2001/0055062 A1 * | 12/2001 | Shioda | .............. | A61B 1/00039 348/79 |
| 2004/0036962 A1 * | 2/2004 | Brunner | ............ | G02B 21/0012 359/368 |
| 2005/0057800 A1 * | 3/2005 | Obrebski | ............... | G02B 7/001 359/385 |
| 2009/0103174 A1 * | 4/2009 | Nozawa | ............ | A61B 1/00149 359/376 |

(Continued)

FOREIGN PATENT DOCUMENTS

| | | |
|---|---|---|
| JP | 2004-117596 | 4/2004 |
| JP | 2016-59499 | 4/2016 |

*Primary Examiner* — Thong Q Nguyen
(74) *Attorney, Agent, or Firm* — Xsensus LLP

(57) ABSTRACT

There is provided a medical observation device including: a microscope unit that includes an image sensor and images an operative site; and a holding unit that holds the microscope unit on a front end side. The holding unit includes a first rotation axis unit that supports the microscope unit to allow rotation about a first rotation axis substantially aligned with an optical axis of the microscope unit. From the microscope unit, a cable group including at least a signal cable that transmits a signal related to the image sensor and a light guide that guides illuminating light for imaging is run towards an outside through an interior of a housing of the first rotation axis unit.

10 Claims, 10 Drawing Sheets

(56) References Cited

U.S. PATENT DOCUMENTS

2017/0227753 A1* 8/2017 Kamata ................. G02B 21/24
2019/0015175 A1* 1/2019 Tamura ................. G02B 21/32

* cited by examiner

MEDICAL OBSERVATION DEVICE AND MEDICAL OBSERVATION SYSTEM

CROSS REFERENCE TO RELATED APPLICATIONS

This application claims the benefit of Japanese Priority Patent Application JP 2016-183964 filed Sep. 21, 2016, the entire contents of which are incorporated herein by reference.

BACKGROUND

The present disclosure relates to a medical observation device and a medical observation system.

In surgical operations targeting a fine region (also called microsurgery), such as neurosurgery, for example, an observation device for enlarged stereoscopic observation of the operative site is used. The observation device includes a microscope unit held by an arm unit (holding unit) (see JP 2004-117596A, for example). The microscope unit of the observation device described in JP 2004-117596A is of an optical type, and the surgeon observes the operative site directly by peering into the microscope unit from an eyepiece provided on the microscope unit. Hereinafter, an observation device provided with an optical microscope unit will also be called an optical observation device.

Meanwhile, in recent years, there are being developed observation devices provided with an image sensor and an electronic imaging microscope unit capable of imaging the operative site electronically (see JP 2016-59499A, for example). With an observation device provided with an electronic imaging microscope unit (hereinafter also called an electronic imaging observation device), a picture of the operative site imaged by the microscope unit is displayed on a display device installed in front of the surgeon. The surgeon then performs surgery while observing the operative site via the picture depicted on the display device. At this time, the microscope unit may be positioned substantially directly above the operative site, or in other words, between the surgeon and the display device. Consequently, there is demand for an electronic imaging microscope unit to be as compact as possible, so as not to obstruct the field of view of the surgeon viewing the display device.

SUMMARY

For an electronic imaging microscope unit, a configuration in which an image sensor is disposed inside a housing having a substantially hollow round cylindrical shape is typical. Also, to adjust the direction of the picture imaged by the microscope unit, the central axis of the hollow round cylindrical shape may be configured to substantially match the optical axis, and the microscope unit may be configured to be rotatable about the optical axis. Specifically, on the base end of the microscope unit, a rotation axis unit (typically called the first rotation axis unit) that rotatably supports the microscope unit may be provided. To ensure the surgeon's field of view, the microscope unit as well as the first rotation axis unit are demanded to be compact. Note that in this specification the size of the microscope unit and the first rotation axis unit is also described using phrases such as "the size of the microscope unit as a whole" for the sake of convenience.

Meanwhile, a cable for transmitting picture signals acquired by the image sensor and control signals for driving the image sensor (hereinafter also called the signal cable) is run from the image sensor provided inside the housing of the microscope unit, towards the outside of the microscope unit. The signal cable may be run from the microscope unit, through the interior of the housing of the first rotation axis unit, along the holding unit, and up to a main unit provided on the base end of the holding unit. At this time, since the signal cable rotates and moves in response to the rotation of the microscope unit about the optical axis described above, it is necessary to provide enough space inside the housing of the microscope unit and the first rotation axis unit to allow the signal cable to move in association with the rotation of the microscope unit about the optical axis. Consequently, to configure the microscope unit compactly as a whole, it is necessary to decrease this space further, and the method of running the signal cable inside the housing of the microscope unit and the first rotation axis unit becomes an important factor.

Regarding this point, in the configuration described in JP 2016-59499A, the signal cable is run along the central axis of the hollow round cylindrical housing of the microscope unit and the first rotation axis unit, or in other words, along the rotation axis of the microscope unit (see JP 2016-59499A, FIG. 3 and the like). According to such a configuration, as the microscope unit rotates about the optical axis, the signal cable is twisted around the central axis of the signal cable, and the signal cable does not move much. Consequently, it is not necessary to secure a large space for the movement of the signal cable inside the housing of the microscope unit and the first rotation axis unit, thus contributing to the compactness of the microscope unit as a whole.

Meanwhile, during imaging by the microscope unit, to image an operative site inside a dark body cavity, for example, in some cases imaging is conducted while shining illuminating light onto the operative site. For this reason, a light guide for guiding illuminating light from an external light source device to the front end of the microscope unit may be run inside the housing of the microscope unit and the first rotation axis unit. With regard to the light guide, similarly to the signal cable described above, it is necessary to consider space inside the housing of the microscope unit and the first rotation axis unit for movement in association with the rotation of the microscope unit about the optical axis. However, such a light guide is not mentioned in JP 2016-59499A.

If the configuration described in JP 2016-59499A is applied as-is, it is anticipated that the light guide, together with the signal cable, will be run along the rotation axis of the microscope unit inside the housing of the microscope unit and the first rotation axis unit. Herein, typically, by using a cable such as a thin-line coaxial cable for the signal cable, for example, it is possible to make the cable diameter comparatively thin, but the diameter of the light guide is thick compared to the signal cable. Consequently, in a case of running both the signal cable and the light guide along the rotation axis of the microscope unit as described above, the cross-sectional area of the cable group that is twisted in response to the rotation of the microscope unit becomes extremely large compared to the case of the signal cable only. Thus, to absorb twists, it is necessary to secure a longer distance over which the cable group is run along the rotation axis, and the length in the rotation axis direction of the housing of the microscope unit and the first rotation axis unit becomes longer. In other words, the attempt to make the microscope unit more compact as a whole becomes difficult.

In this case, in the case in which a light guide is also considered, from the perspective of making the microscope unit more compact as a whole, there is a possibility that the method of running a cable group in the technology described in JP 2016-59499A may not necessarily be appropriate. By making innovations with respect to the method of running the cable group, the microscope unit can be made more compact as a whole, and there is a possibility of ensuring the surgeon's field of view more favorably.

Accordingly, the present disclosure proposes a new and improved medical observation device and medical observation system capable of ensuring a better field of view for the surgeon.

According to an embodiment of the present disclosure, there is provided a medical observation device including: a microscope unit that includes an image sensor and images an operative site; and a holding unit that holds the microscope unit on a front end side. The holding unit includes a first rotation axis unit that supports the microscope unit to allow rotation about a first rotation axis substantially aligned with an optical axis of the microscope unit. From the microscope unit, a cable group including at least a signal cable that transmits a signal related to the image sensor and a light guide that guides illuminating light for imaging is run towards an outside through an interior of a housing of the first rotation axis unit. The cable group is run, at a position that does not match the first rotation axis when facing from the microscope unit towards the interior of the housing of the first rotation axis unit, in a direction substantially parallel to the first rotation axis, and run in a direction substantially parallel to a plane that is orthogonal to the first rotation axis in the interior of the housing of the first rotation axis unit.

Further, according to an embodiment of the present disclosure, there is provided a medical observation system including: a medical observation device including a microscope unit that includes an image sensor and images an operative site, and a holding unit that holds the microscope unit on a front end side; and a display device that displays a picture imaged by the medical observation device. In the medical observation device, the holding unit includes a first rotation axis unit that supports the microscope unit to allow rotation about a first rotation axis substantially aligned with an optical axis of the microscope unit, from the microscope unit, a cable group including at least a signal cable that transmits a signal related to the image sensor and a light guide that guides illuminating light for imaging is run towards an outside through an interior of a housing of the first rotation axis unit, and the cable group is run, at a position that does not match the first rotation axis when facing from the microscope unit towards the interior of the housing of the first rotation axis unit, in a direction substantially parallel to the first rotation axis, and run in a direction substantially parallel to a plane that is orthogonal to the first rotation axis in the interior of the housing of the first rotation axis unit.

According to an embodiment of the present disclosure, in an observation device in which a microscope unit is held by an arm unit (holding unit), when a cable group is run from the microscope unit towards the outside through the interior of a housing of a first rotation axis unit, the cable group is run, at a position that does not match a first rotation axis which substantially matches the optical axis of the microscope unit when facing from the microscope unit towards the interior of the housing of the first rotation axis unit, in a direction substantially parallel to the first rotation axis, and is run in a direction substantially parallel to a plane that is orthogonal to the first rotation axis inside the housing of the first rotation axis unit. Consequently, when the microscope unit rotates about the first rotation axis, the cable group moves to bend in the horizontal plane. Consequently, since it is not necessary to provide enough space in the height direction of the microscope unit and the first rotation axis unit to allow movement of the cable in association with the rotation of the microscope unit about the first rotation axis, the height of the microscope unit and the first rotation axis unit can be made shorter. Thus, a more compact microscope unit as a whole can be realized, thereby making it possible to secure a better field of view for the surgeon.

According to an embodiment of the present disclosure as described above, it becomes possible to secure a better field of view for the surgeon. Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
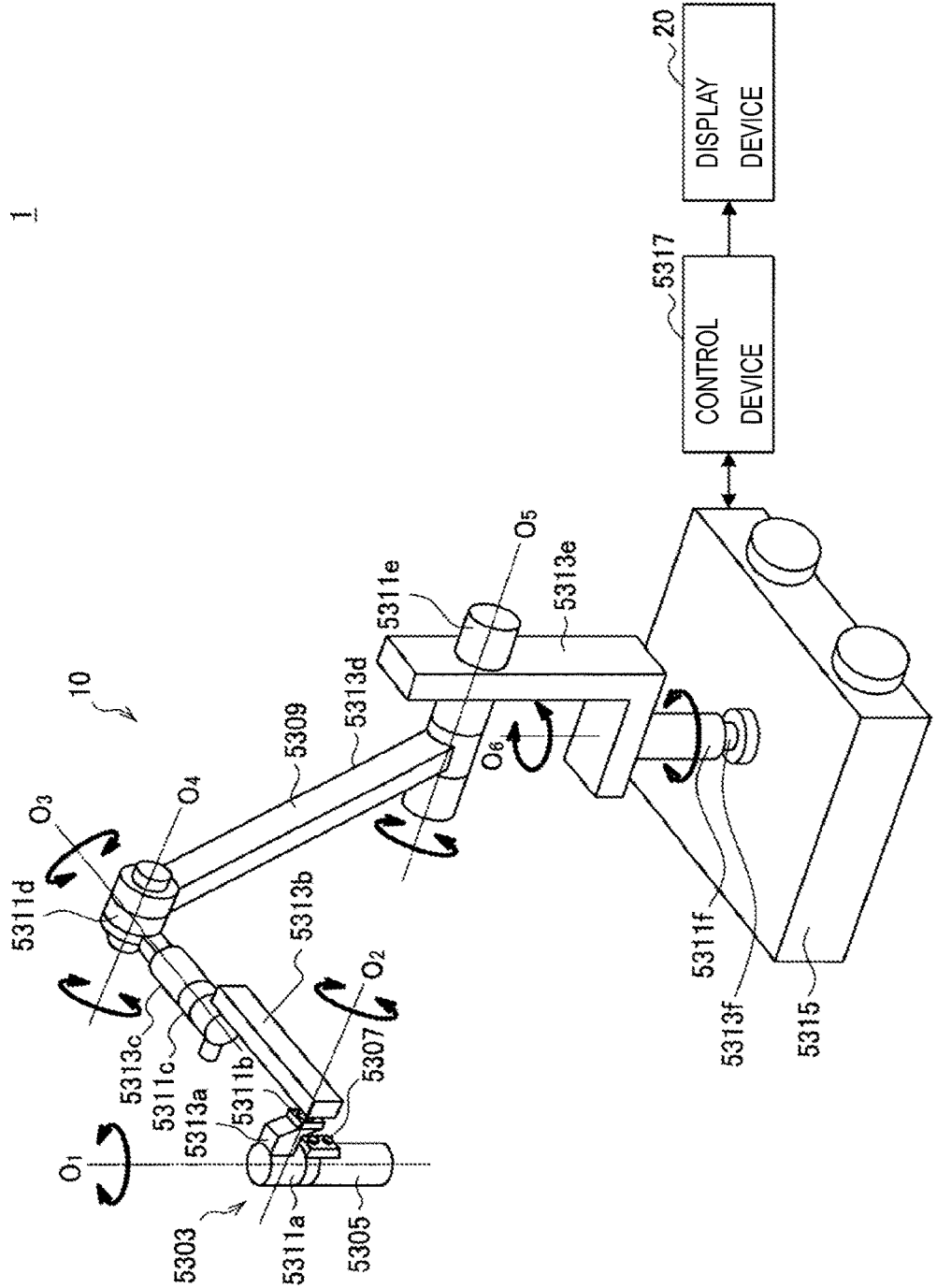
FIG. 1 is a diagram that schematically illustrates one exemplary configuration of an observation system and an observation device according to an embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that in each of the diagrams illustrated in this specification, the apparent sizes of some component members are exaggerated in some cases for the sake of explanation. The relative sizes of the respective members illustrated in each of the drawings do not necessarily represent accurately the size relationships among actual members.

Hereinafter, the description will proceed in the following order.

1. Configuration of observation system and observation device
2. Configuration of microscope unit and first rotation axis unit
3. Operation during use
4. Modifications
4-1. Modification provided with partitioning plate
4-2. Another exemplary configuration of cable group running space
5. Method of running cable group in other parts of holding unit
6. Supplemental remarks (1. Configuration of Observation System and Observation Device)

A configuration of an observation system and an observation device according to an embodiment of the present disclosure will be described with reference to FIG. 1. FIG. 1 is a diagram that schematically illustrates one exemplary configuration of an observation system and an observation device according to an embodiment.

Referring to FIG. 1, an observation system 1 according to the present embodiment includes an electronic imaging observation device 10 enabling enlarged observation of an operative site of a patient, and a display device 20 that displays a picture of the operative site imaged by the observation device 10. The observation system 1 is a medical observation system for observing a part of the patient's body, namely, an observation target site (a surgery target site (operative site) or an examination target site) when performing a medical procedure such as a surgery or an examination. During the surgery or examination, the surgeon observes the observation target site via a picture imaged by the observation device 10 and displayed on the display device 20, and performs various treatments on the observation target site as necessary. Hereinafter, the case of using the observation system 1 to perform surgery will be described as an example, and the observation target site will also be called the operative site.

(Display Device)

The display device 20, under control by a control device 5317 of the observation device 10 described later, displays a picture of an operative site of a patient imaged by the observation device 10. The display device 20 is installed in a location visible to the surgeon inside the operating room, such as on a wall of the operating room, for example. The type of the display device 20 is not particularly limited, and any of various known types of display devices may be used as the display device 20, such as a cathode ray tube (CRT) display device, a liquid crystal display device, a plasma display device, or an electroluminescence (EL) display device. Additionally, the display device 20 is not necessarily required to be installed inside the operating room, and may also be installed in a device used by being worn on the surgeon's body, such as a head-mounted display (HMD) or an eyeglasses-type wearable device.

Note that, as described later, in a case in which an imaging unit of a microscope unit 5303 of the observation device 10 is configured as a stereo camera, or configured to be capable of high-resolution imaging, for example, a corresponding display device 20 capable of 3D display or high-resolution display may be used.

(Observation Device)

The observation device 10 is provided with a microscope unit 5303 for performing enlarged observation of the surgical site of the patient, an arm unit 5309 (holding unit 5309) that holds the microscope unit 5303, a base unit 5315 to which the base end of the holding unit 5309 is connected and which supports the microscope unit 5303 and the holding unit 5309, and a control device 5317 that controls the operation of the observation system 1 and the observation device 10.

Note that in the following description, the vertical direction with respect to the floor on which the observation device 10 is installed is defined to be the z-axis direction. The z-axis direction is also called the up-and-down direction. Also, the direction which is orthogonal to the z-axis direction and in which the holding unit 5309, when parallel to the floor, extends from the base unit 5315 is defined to be the x-axis direction. The x-axis direction is also called the forward-and-backward direction. Also, the direction orthogonal to both the x-axis direction and the z-axis direction is defined to be the y-axis direction. The y-axis direction is also called the left-and-right direction. Additionally, a plane parallel to the x-y plane is also called the horizontal plane, while a direction parallel to the horizontal plane is also called a horizontal direction.

(Base Unit)

The base unit 5315 supports the microscope unit 5303 and the holding unit 5309. The base unit 5315 includes a platform having a planar shape, and multiple casters provided on the bottom face of the platform. One end of the holding unit 5309 is connected to the top face of the platform, while the microscope unit 5303 is connected to the other end of the holding unit 5309 extending from the platform (the front end). Also, the observation device 10 is in contact with the floor through the casters, and is configured to be movable across the floor by the casters.

(Microscope Unit)

The microscope unit 5303 is an electronic imaging microscope unit. In the illustrated example, the optical axis direction of the microscope unit 5303 is substantially aligned with the z-axis direction. The microscope unit 5303 includes a barrel unit 5305, which is a housing having a substantially hollow round cylindrical shape, and an imaging unit (not illustrated) provided inside the barrel unit 5305.

Light from an observation target (observation light) enters the imaging unit from an aperture on the bottom end of the barrel unit 5305. The imaging unit includes an image sensor and an optical system that condenses observation light onto the image sensor. Observation light entering the imaging unit is condensed onto the photosensitive face of the image sensor through the optical system. By photoelectrically converting the observation light with the image sensor, a signal corresponding to a picture of the subject (picture signal) is acquired. The picture signal acquired by the imaging unit is transmitted to the control device 5317. Note that the configuration inside the barrel unit 5305 of the microscope unit 5303, such as the imaging unit, will be described in further detail in (2. Configuration of microscope unit and first rotation axis unit) below.

In the microscope unit 5303, an operating unit 5307 for controlling the operation of the microscope unit 5303 is provided on the outer wall of the barrel unit 5305. The operating unit 5307 includes elements such as a directional lever or switches, for example.

For example, via the operating unit 5307, the surgeon is able to input an instruction to change the magnification factor and the focus distance of the microscope unit 5303.

The above imaging unit is provided with a driving mechanism that drives a zoom lens and a focus lens included in the above optical system in the optical axis direction, and by having the driving mechanism appropriately move the zoom lens and the focus lens in accordance with instructions input via the operating unit 5307, the magnification factor and the focus distance may be adjusted.

As another example, via the operating unit 5307, the surgeon is able to input an instruction to toggle the operating mode of the holding unit 5309 to either a free mode or a locked mode. Herein, the locked mode is an operating mode in which the position and the attitude of the microscope unit 5303 are locked by using a brake to restrain rotation about each rotation axis of the holding unit 5309. The free mode is an operating mode in which the brake is released, thereby allowing free rotation about each rotation axis of the holding unit 5309. For example, in the free mode, the position and the attitude of the microscope unit 5303 are adjustable by direct operations performed by the surgeon. Herein, direct operations mean operations in which the surgeon grips the microscope unit 5303 with his or her hand, and directly moves the microscope unit 5303. For example, the operating mode of the holding unit 5309 becomes the free mode while the surgeon is holding down an operating mode toggle switch on the operating unit 5307, and the operating mode of the holding unit 5309 becomes the locked mode while the surgeon releases his or her hand from the toggle switch.

Note that, as described above, in a case in which the surgeon attempts to move the microscope unit 5303, it is anticipated that the surgeon moves the barrel unit 5305 with direct operations, or in other words by gripping and holding the barrel unit 5305. Consequently, the operating unit 5307 preferably is provided at a position that allows easy operation with the fingers while the surgeon is gripping the barrel unit 5305, to thereby allow the surgeon to operate the operating unit 5307 even while moving the barrel unit 5305.

(Holding Unit)

The holding unit 5309 moves the microscope unit 5303 three-dimensionally, while also securely supporting the position and the attitude of the microscope unit 5303 after moving. In the present embodiment, the holding unit 5309 is configured as an arm having six degrees of freedom. However, the present embodiment is not limited to such an example, and the holding unit 5309 may also be configured to have a different number of degrees of freedom, insofar as the holding unit 5309 is configured sufficiently to allow the microscope unit 5303 to move appropriately according to the intended purpose.

The holding unit 5309 is provided with six rotation axes corresponding to the six degrees of freedom (first axis $O_1$, second axis $O_2$, third axis $O_3$, fourth axis $O_4$, fifth axis $O_5$, and sixth axis $O_6$). In the following description, for the sake of convenience, the members constituting each rotation axis will be referred to collectively as the rotation axis unit. For example, the rotation axis unit may include components such as a bearing, a shaft rotatably inserted into the bearing, and a brake that restrains rotation about the rotation axis.

The holding unit 5309 is configured as a result of multiple links (a first arm unit 5313a to a sixth arm unit 5313f being rotatably joined to each other by multiple rotation axis units (a first rotation axis unit 5311a to a sixth rotation axis unit 5311f) corresponding to six rotation axes.

The first rotation axis unit 5311a has a substantially cylindrical shape, the front end (bottom end) of which supports the top end of the barrel unit 5305 of the microscope unit 5303, so as to allow rotation about a rotation axis (first axis $O_1$) parallel to the central axis of the barrel unit 5305. Herein, the first joint unit 5311a may be configured so that the first axis $O_1$ is aligned with the optical axis of the imaging unit of the microscope unit 5303. With this arrangement, rotating the microscope unit 5303 about the first axis $O_1$ makes it possible to change the field of view as though rotating the captured image.

The first arm unit 5313a securely supports the first rotation axis unit 5311a on the front end thereof. Specifically, the first arm unit 5313a is a substantially L-shaped rod-like member, the front edge of which extends in a direction orthogonal to the first axis $O_1$, while also being connected to the first rotation axis unit 5311a so that the end of that edge abuts the top end on the outer circumference of the first rotation unit 5311a. The second rotation axis unit 5311b is connected to the end of the base edge of the approximate L-shape of the first arm unit 5313a.

The second rotation axis unit 5311b has a substantially cylindrical shape, and on the front end thereof supports the base end of the first arm unit 5313a, so as to allow rotation about a rotation axis (second axis $O_2$) orthogonal to the first axis $O_1$. The front end of the second arm unit 5313b is securely connected to the base end of the second rotation axis unit 5311b.

The second arm unit 5313b is a substantially L-shaped rod-like member, the front edge of which extends in a direction orthogonal to the second axis $O_2$, while the end of that edge is securely connected to the base end of the second rotation axis unit 5311b. The third rotation axis unit 5311c is connected to the base edge of the approximate L-shape of the second arm unit 5313b.

The third rotation axis unit 5311c has a substantially cylindrical shape, and on the front end thereof supports the base end of the second arm unit 5313b, so as to allow rotation about a rotation axis (third axis $O_3$) orthogonal to both the first axis $O_1$ and the second axis $O_2$. The front end of the third arm unit 5313c is securely connected to the base end of the third rotation axis unit 5311c. By rotating the configuration on the front-end side, including the microscope unit 5303, about the second axis $O_2$ and the third axis $O_3$, the microscope unit 5303 can be moved to change the position of the microscope unit 5303 in the horizontal plane. In other words, controlling the rotation about the second axis $O_2$ and the third axis $O_3$ makes it possible to move the field of view of the captured image on a flat plane.

The third arm unit 5313c is configured to have a substantially cylindrical shape on the front end side, and on the front end of the cylindrical shape, the base end of the third rotation axis unit 5311c is securely connected so that both have substantially the same central axis. The base end side of the third arm unit 5313c has a rectangular column shape, and the fourth rotation axis unit 5311d is connected to the end thereof.

The fourth rotation axis unit 5311d has a substantially cylindrical shape, and on the front end thereof supports the base end of the third arm unit 5313c, so as to allow rotation about a rotation axis (fourth axis $O_4$) orthogonal to the third axis $O_3$. The front end of the fourth arm unit 5313d is securely connected to the base end of the fourth rotation axis unit 5311d.

The fourth arm unit 5313d is a rod-like member that extends substantially linearly in a direction orthogonal to the fourth axis $O_4$, while also being securely connected to the fourth rotation axis unit 5311d so that the front end abuts the side face of the substantially cylindrical shape of the fourth rotation axis unit 5311d. The fifth rotation axis unit 5311e is connected to the base end of the fourth arm unit 5313d.

The fifth rotation axis unit 5311e has a substantially cylindrical shape, and on the front end side thereof supports the base end of the fourth arm unit 5313d, so as to allow rotation about a rotation axis (fifth axis $O_5$) parallel to the fourth axis $O_4$. The front end of the fifth arm unit 5313e is securely connected to the base end of the fifth rotation axis unit 5311e. The fourth axis $O_4$ and the fifth axis $O_5$ are rotation axes enabling the microscope unit 5303 to be moved in the up-and-down direction. By rotating the configuration on the front-end side, including the microscope unit 5303, about the fourth axis $O_4$ and the fifth axis $O_5$, the height of the microscope unit 5303, or in other words the distance between the microscope unit 5303 and the observation target, can be adjusted.

The fifth arm unit 5313e includes a combination of a first member having an approximate L-shape with one edge extending in the vertical direction while the other edge extends in the horizontal direction, and a rod-like second member that extends vertically downward from the part of the first member that extends in the horizontal direction. The base end of the fifth rotation axis unit 5311e is securely connected near the top end of the part of the first member that extends in the vertical direction in the arm unit link 5313e. The sixth rotation axis unit 5311f is connected to the base end (bottom end) of the second member of the fifth arm unit 5313e.

The sixth rotation axis unit 5311f has a substantially cylindrical shape, and on the front end side thereof supports the base end of the fifth arm unit 5313e, so as to allow rotation about a rotation axis (sixth axis $O_6$) parallel to the vertical direction. The front end of the sixth arm unit 5313f is securely connected to the base end of the sixth rotation axis unit 5311f.

The sixth arm unit 5313f is a rod-like member that extends in the vertical direction, with the base end securely connected to the top face of the base unit 5315.

The allowable rotation range of the first rotation axis unit 5311a to the sixth rotation axis unit 5311f is suitably set so that the microscope unit 5303 is capable of desired movement. With this arrangement, in the holding unit 5309 having the configuration described above, three degrees of translational freedom and three degrees of rotational freedom, for a total of six degrees of freedom, may be realized for the motion of the microscope unit 5303. In this way, by configuring the holding unit 5309 so that six degrees of freedom are realized for the motion of the microscope unit 5303, it becomes possible to freely control the position and the attitude of the microscope unit 5303 within the movable range of the holding unit 5309. Consequently, it becomes possible to observe the operative site from any angle, and surgery may be executed more smoothly.

Each of the first rotation axis unit 5311a to the sixth rotation axis unit 5311f of the holding unit 5309 is provided with a brake that restrains rotation in the first rotation axis unit 5311a to the sixth rotation axis unit 5311f, respectively. The driving of these brakes is controlled by the control device 5317. By releasing these brakes all at once under control from the control device 5317, the operating mode of the holding unit 5309 switches to the free mode. Also, by driving these brakes all at once under similar control from the control device 5317, the operating mode of the holding unit 5309 switches to the locked mode.

Note that for the brakes provided in the first rotation axis unit 5311a to the sixth rotation axis unit 5311f, any of various types of brakes used in a typical observation device may be applied, and the specific mechanism is not limited. For example, these brakes may be mechanically driven, or may also be electrically driven electromagnetic brakes.

Note that the configuration of the holding unit 5309 illustrated in the diagram is merely one example, and factors such as the number and the shapes (lengths) of the links constituting the holding unit 5309, as well as the number and arrangement of the rotation axis units and the directions of the rotation axes may be designed suitably so that the desired degrees of freedom may be realized. However, as described above, to move the microscope unit 5303 freely, the holding unit 5309 preferably is configured to have at least six degrees of freedom.

(Control Device)

The control device 5317 controls the operation of the observation device 10. In addition, the control device 5317 also controls the operation of the display device 20 at the same time. In other words, the control device 5317 may centrally control the operation of the observation system 1.

The control device 5317 includes a processor such as a central processing unit (CPU) or a digital signal processor (DSP), or a control board or the like on which these processors are mounted together with a storage element such as memory. As a result of the processor constituting the control device 5317 executing computational processing in accordance with a predetermined program, the respective functions of the control device 5317 are realized.

The control device 5317 includes a function of toggling the operating mode of the holding unit 5309 described earlier by controlling the driving of the brake provided in each rotation axis unit of the holding unit 5309 in response to operating input performed by the surgeon via the operating unit 5307 described earlier. Also, the control device 5317 includes a function of appropriately driving the optical system in the imaging unit of the microscope unit 5303 to adjust the magnification and the focus distance of the microscope unit 5303 in response to operating input performed by the surgeon via the operating unit 5307 described earlier.

In addition, the control device 5317 conducts various types of image processing on a picture signal transmitted from the imaging unit of the microscope unit 5303, such as a gamma correction process, a white balance adjustment process, an enlargement process related to an electronic zoom function, and a pixel interpolation process, for example. For the image processing, any of various types of image processing typically conducted to display a picture on the display device 20 may be conducted. The control device 5317 transmits the picture signal that has been subjected to various types of image processing to the display device 20, and causes the display device 20 to display a picture imaged by the microscope unit 5303. Note that the communication between the control device 5317 and the display device 20 may be realized by any of various known types of wired or wireless methods.

The above thus describes a configuration of the observation system 1 and the observation device 10 according to the present embodiment with reference to FIG. 1. Note that the configuration of the observation device 10 according to the present embodiment is not limited to the above-described. As described below, the observation device 10 according to the present embodiment includes a characteristic configuration with regard to the method of running of a cable group 116 from the microscope unit 5303 towards the outside. Points regarding the configuration of the observation device 10 other than such a method of running the cable group 116 may be arbitrary, and any of various known types of configurations may be applied.

(2. Configuration of Microscope Unit and First Rotation Axis Unit)

Figure 2:
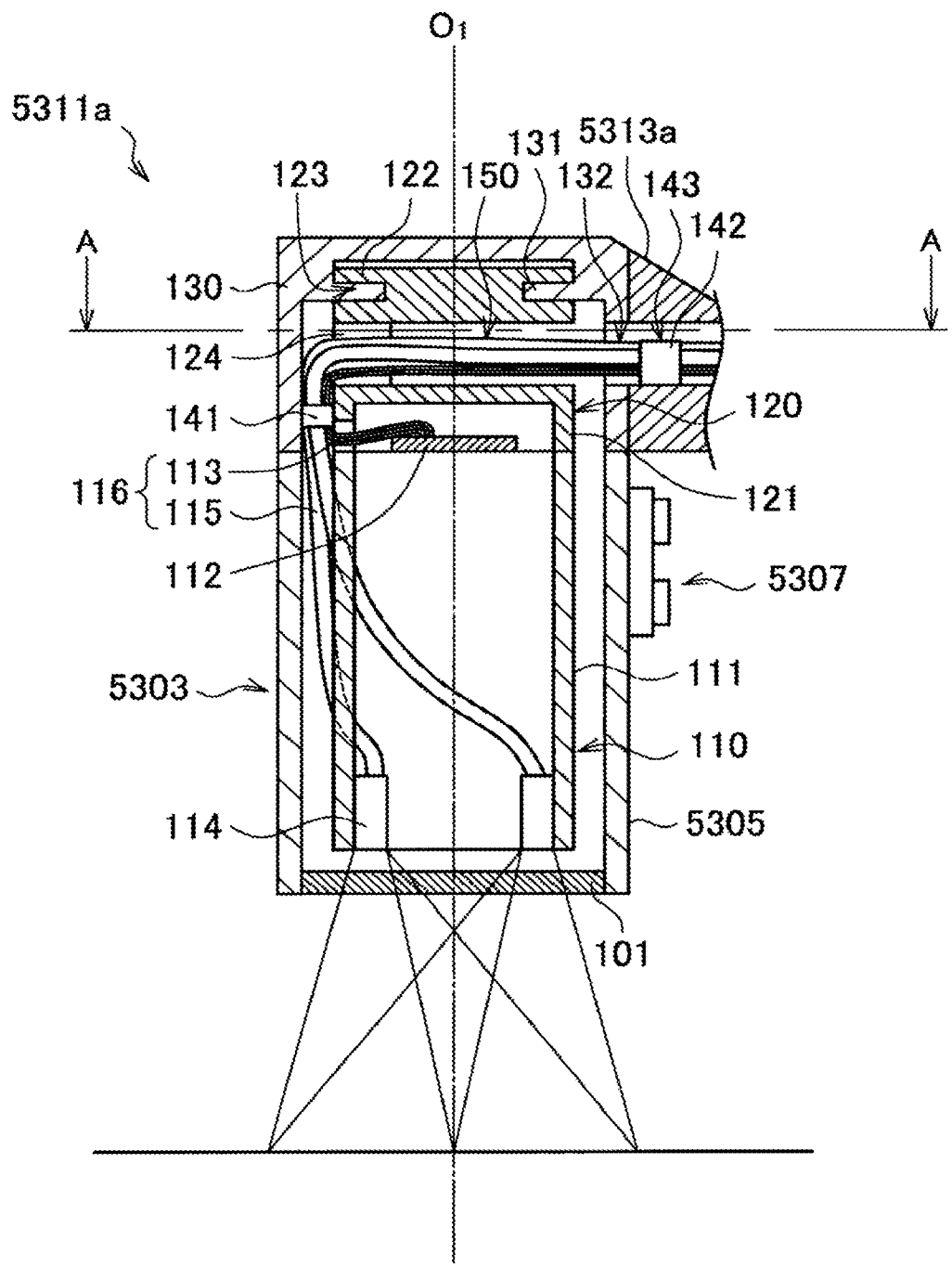
FIG. 2 is a cross section diagram that schematically illustrates the configuration around a microscope unit and a first rotation axis unit.
Figure 3:
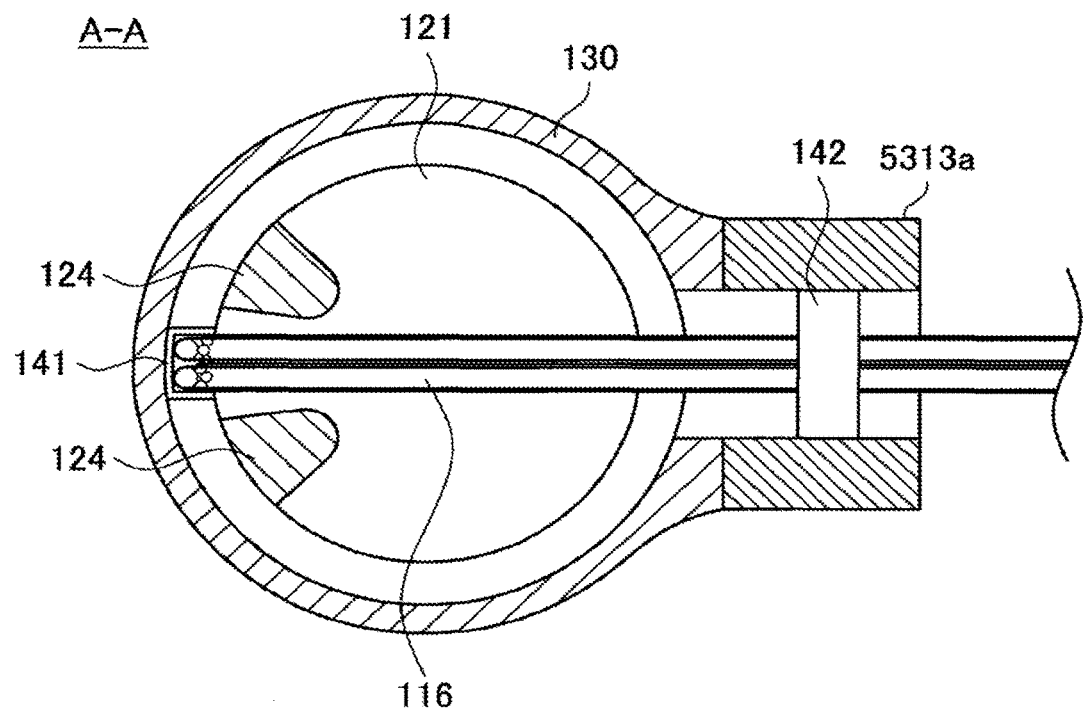
FIG. 3 is a cross section diagram along the A-A cross section illustrated in FIG. 2 of the configuration around a microscope unit and a first rotation axis unit.

The configuration of the microscope unit 5303 and the first rotation axis unit 5311a described above will be described in further detail with reference to FIGS. 2 and 3. FIG. 2 is a cross section diagram that schematically illustrates the configuration around the microscope unit 5303 and the first rotation axis unit 5311a. FIG. 2 illustrates a cross section, taken along the optical axis, of the configuration around the microscope unit 5303 and the first rotation axis unit 5311a. FIG. 3 is a cross section, taken along the A-A cross section illustrated in FIG. 2, of the configuration around the microscope unit 5303 and the first rotation axis unit 5311a.

As illustrated in FIG. 2, the microscope unit 5303 includes a barrel unit 5305, which is a hollow round cylindrical housing, and an imaging unit 110 provided inside the barrel unit 5305. The aperture on the bottom end of the barrel unit 5305 is provided with a cover glass 101 for protecting the imaging unit 110 inside. During imaging, observation light enters the imaging unit 110 through the cover glass 101.

The imaging unit includes a hollow round cylindrical housing 111, an image sensor 112, an optical system (not illustrated) that condenses observation light onto the image sensor 112, and an illumination unit 114 that radiates illuminating light onto the observation target.

The housing 111 has a smaller diameter than the barrel unit 5305, and is disposed inside the barrel unit 5305 to be substantially coaxial with the barrel unit 5305. Note that the housing 111 is securely connected to the barrel unit 5305, and when the microscope unit 5303 rotates about the first axis $O_1$, the housing 111 (that is, the imaging unit 110) and the barrel unit 5305 also rotate.

The image sensor 112 is disposed on the top end of the housing 111, in a state by which the photosensitive face faces downward. Any of various known types of image sensors may be applied as the image sensor 112, such as a charge-coupled device (CCD) sensor or a complementary metal-oxide-semiconductor (CMOS) sensor, for example. Observation light is condensed onto the photosensitive face of the image sensor 112 and photoelectrically converted, and thus a picture signal is acquired by the image sensor 112.

Inside the housing 111, an optical system not illustrated is disposed below the image sensor 112. Observation light entering the imaging unit 110 through the cover glass 101 passes through the optical system to reach the photosensitive face of the image sensor 112. The optical system includes various types of lenses, such as an objective lens, a zoom lens, and a focus lens, as well as optical elements such as a mirror, in which the optical characteristics and placement of each are adjusted to condense observation light onto the photosensitive face of the image sensor 112. Note that, as described above, a driving mechanism may be provided to move the position of the zoom lens and the focus lens on the optical axis in order to adjust the magnification and the focus distance.

Inside the housing 111, the illumination unit 114 is disposed on the bottom end. A light guide 115 running from an external light source device is connected to the illumination unit 114, and during imaging, illuminating light is radiated onto the observation target from the illumination unit 114. In the illustrated example, two illumination units 114 are provided, but the present embodiment is not limited to such an example, and the installed number and installed positions of illumination units 114 may be decided appropriately so that illuminating light is radiated onto the observation target uniformly.

Note that the configuration of the imaging unit 110 is not limited to the illustration, and a configuration used in any of various known types of electronic imaging microscope units may also be applied as the imaging unit 110. For example, the imaging unit 110 may also be configured as a stereo camera equipped with a pair of image sensors to support 3D display. Alternatively, the imaging unit 110 may be configured to be able to take images at a high resolution, such as 4K or 8K, for example. By having the imaging unit 110 take images supporting 3D display or take images at a high resolution, it becomes possible to improve visibility for the surgeon who looks at the picture imaged by the imaging unit 110. Also, any of various types of functions typically provided in electronic imaging microscope units, such as an autofocus (AF) function and an auto exposure (AE) function, may be provided in the imaging unit 110.

The first rotation axis unit 5311a includes a first rotation member 120 which is disposed on the top end (base end) of the imaging unit 110 and which securely supports the imaging unit 110 (in other words, disposed on the base end of the microscope unit 5303, and securely supports the microscope unit 5303), and a second rotation member 130 which is disposed to cover the first rotation member 120 and which supports the first rotation member 120 to allow rotation about the first axis $O_1$. In other words, when the microscope unit 5303 rotates about the first axis $O_1$, the first rotation member 120, the imaging unit 110, and the barrel unit 5305 also rotate in a state of being supported by the second rotation member 130.

The first rotation member 120 includes a first member 121 which is connected to the top end (base end) of the housing 111 of the imaging unit 110, and which has a substantially hollow round cylindrical shape with a floor on one end, a substantially disc-shaped second member 122 disposed above the first member 121 at a predetermined interval from the first 121, and a columnar connecting member 124 that connects the first member 121 and the second member 122 in the up-and-down direction.

The first member 121 is connected to the housing 111 of the imaging unit 110 so that the open part faces downward, or in other words, faces towards the imaging unit 110, while the floored part faces upward. In other words, the first member 121 is provided to cover the top part of the housing 111. The first member 121 also fulfills a role of protecting the image sensor 112. The first member 121 is configured to have a hollow round cylindrical shape of substantially equal diameter to the housing 111, and is securely connected to the top end of the housing 111. Also, the first member 121 is configured so that when connected to the housing 111, the floored part is substantially parallel to the horizontal plane.

The second member 122 is substantially disc-shaped, with the bottom face disposed above the first member 121 so as to face opposite the top face of the first member 121 (in other words, the floored part described above) at a predetermined interval. The second member 122 is disposed so that at least the bottom face is substantially parallel to the horizontal plane. The side face of the second member 122 is provided with a groove 123 along the circumferential direction. An engaging part 131 described later, which is provided on the inner wall of the second rotation member 130, freely fits into this groove 123. According to such a configuration, the second member 122 is rotatably supported by the second rotation member 130, with the up-and-down direction (in other words, the first axis $O_1$) taken as the rotation axis.

The connecting member 124 is interposed between the top face of the first member 121 and the bottom face of the second member 122, and securely connects the two. The connecting member 124 is configured so that the cross-sectional area in the horizontal plane is sufficiently small compared to the area of the top face of the first member 121 and the area of the bottom face of the second member 122. In other words, the connecting member 124 is interposed only in a partial region between the top face of the first member 121 and the bottom face of the second member 122. According to such a configuration, a substantially disc-shaped space 150 in which only the connecting member 124 exists is formed between the top face of the first member 121 and the bottom face of the second member 122 (since the cable group 116 described later is run through this space, hereinafter, the space 150 is also called the cable group running space 150). Note that details about the number, arrangement, and shape of the connecting member 124 will be described later.

The second rotation member 130 has a substantially hollow round cylindrical shape with a floor on one end, and of substantially equal diameter to the barrel unit 5305. The second rotation member 130 is disposed on the top part of the barrel unit 5305 so that the open part faces downward and the floored part faces upward. In other words, the second rotation member 130 is disposed to cover the outer circumference and top of the first rotation member 120. Note that the second rotation member 130 and the barrel unit 5305 are not connected securely, and the barrel unit 5305 is able to rotate about the first axis $O_1$ with respect to the second rotation member 130.

On the inner wall of the second rotation member 130, at the part that faces opposite the side face of the second member 122 of the first rotation member 120, an engaging part 131 that projects outward towards the second member 122 is provided along the circumferential direction of the inner wall. This engaging part 131 freely fits into the groove 123 provided on the side face of the second member 122 of the first rotation member 120, and as a result, the second member 122, or in other words the first rotation member 120, is supported by the second rotation member 130 so as to allow rotation about the first axis $O_1$.

Additionally, on the outer wall of the second rotation member 130, one end of the first arm unit 5313a is connected securely. In other words, the first rotation axis unit 5311a is supported securely by the first arm unit 5313a.

Herein, multiple signal cables 113 for transmitting a control signal for driving the image sensor 112 and a picture signal acquired by the image sensor 112 are run between the image sensor 112 of the imaging unit 110 and the control device 5317. Also, as described earlier, multiple light guides 115 are run from an external light source device to the illumination unit 114 of the imaging unit 110. These signal cables 113 and light guides 115 (hereinafter called the cable group 116) are run from the microscope unit 5303, along the holding unit 5309, to the base end of the holding unit 5309. Consequently, at the part where one end of the first arm unit 5313a is connected on the side wall of the second rotation member 130, an opening 132 through which the cable group 116 is inserted (hereinafter also called the cable opening 132) is provided. Additionally, space for the insertion of the cable group 116 (hereinafter also called the cable space 143) is also provided inside the first arm unit 5313a. In other words, inside the housing of the microscope unit 5303 and the first rotation axis unit 5311a, the cable group 116 is run from the imaging unit 110 up to the cable opening 132.

Meanwhile, as described earlier, the barrel unit 5305, the imaging unit 110, and the first rotation member 120 are configured to be rotatable about the first axis $O_1$. In the case in which these members rotate about the first axis $O_1$, the cable group 116 also rotates and moves together. At this point, if the cable group 116 moving due to the rotation about the first axis $O_1$ interferes with the internal members, smooth rotation is impeded by the reaction force, and there is a risk of lowered operability of the observation device 10. Also, there is a risk that repeated occurrence of a situation in which the cable group 116 interferes with the internal members due to the rotation about the first axis $O_1$ will lead to damage to the cable group 116, and normal operation of the observation device 10 possibly may be impeded. Consequently, to moderate the occurrence of these faults, there is demand to provide enough space allowing the cable group 116 to move in association with rotation about the first axis $O_1$ inside the housing of the microscope unit 5303 and the first rotation axis unit 5311a.

However, the microscope unit 5303 is an electronic imaging microscope unit, and in the observation system 1, a picture of an operative site imaged by the microscope unit 5303 is depicted on the display device 20. The surgeon then performs surgery while observing the operative site by the picture depicted on the display device 20. At this point, the microscope unit 5303 and the first rotation axis unit 5311a are positioned substantially above the operative site, and may be positioned between the surgeon and the display device 20. Consequently, there is demand for the microscope unit 5303 and the first rotation axis unit 5311a to be more compact, in order to interfere with the surgeon's field of view as little as possible. Particularly, to ensure the surgeon's field of view, it is desirable to make the length in the up-and-down direction (the height) of the microscope unit 5303 and the first rotation axis unit 5311a shorter.

In this way, in the microscope unit 5303 and the first rotation axis unit 5311a, there is demand to configure the microscope unit 5303 and the first rotation axis unit 5311a (the microscope unit 5303 as a whole) more compactly, while also securing space for the movement of the cable group 116 described above.

To meet such demands, in the present embodiment, the cable group 116 is run as follows. Namely, the cable group 116 that extends from the imaging unit 110 to the outside is bundled by a first bundling member 141 at a part of the outer circumference of the first member 121 of the first rotation member 120. Specifically, in the case in which the microscope unit 5303 is at the zero point of rotation about the first axis $O_1$ (in other words, a neutral position that acts as a reference for the rotational angle), the part where the cable group 116 is bundled is a position symmetric with the cable opening 132 about the first axis $O_1$.

Additionally, the cable group 116 bundled by the first bundling member 141 is run over the top face of the first member 121 of the first rotation member 120 in the horizontal direction to the cable opening 132 and the cable space 143. In other words, the cable group 116 is run in the horizontal direction through the substantially disc-shaped cable group running space 150 between the top face of the first member 121 and the bottom face of the second member 122. Herein, in the present embodiment, the first member 121, the second rotation member 130, and the first arm unit 5313a are configured so that the height of the top face of the first member 121 and the height of the bottom end of the cable opening 132 and the cable space 143 are substantially the same height. Consequently, the cable group 116 run in the horizontal direction in the cable group running space 150 is inserted into the cable opening 132 and the cable space 143 while keeping a substantially constant height. Inside the cable space 143, a second bundling member 142 is provided, and the cable group 116 is bundled by the second bundling member 142 in the cable space 143. Note that in the following, the position where the cable group 116 bundled by the first bundling member 141 enters the cable group running space 150 is also called the cable group entry position for the sake of convenience. Also, the position where the cable group 116 exits the cable group running space 150 (that is, a part on the outer circumference of the cable group running space 150 corresponding to the direction in which the cable opening 132 and the cable space 143 exist) is also called the cable group exit position for the sake of convenience.

Figure 4:
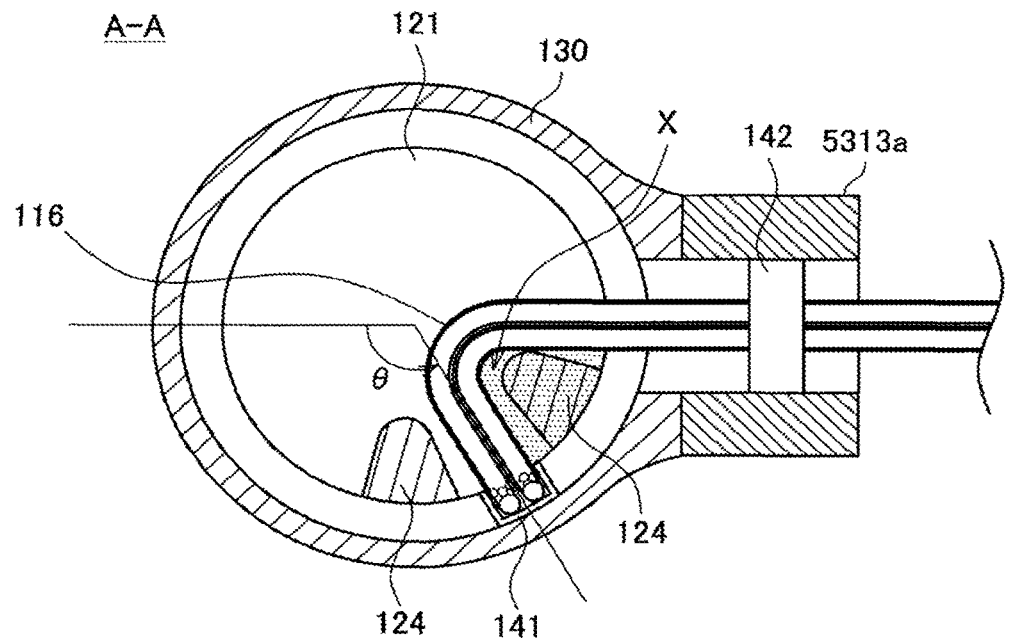
FIG. 4 is a diagram for explaining the movement of a cable group when a microscope unit rotates about a first axis $O_1$.

FIG. 4 is a diagram for explaining the movement of the cable group 116 when the microscope unit 5303 rotates about the first axis $O_1$. According to such a configuration, when the microscope unit 5303 rotates about the first axis $O_1$ (that is, when the barrel unit 5305, the imaging unit 110, and the first rotation member 120 rotate about the first axis $O_1$), as illustrated in FIG. 4, the cable group 116 moves (is bent) in the horizontal plane inside the cable group running space 150. With regard to the configuration around the microscope unit 5303, FIG. 4 illustrates the state in the same cross section as the cross section illustrated in FIG. 3 is illustrated, and illustrates a state in which the microscope unit 5303 has rotated about the first axis $O_1$ by an angle θ counterclockwise from the state illustrated in FIG. 3.

In this way, by limiting the movement of the cable group 116 in association with the rotation of the microscope unit 5303 about the first axis $O_1$ to movement in the horizontal direction, not much space in the height direction is demanded of the space for allowing the movement of the cable group 116. In other words, the space for allowing the movement of the cable group 116 in association with rotation about the first axis $O_1$ can be formed as a flat space with a short length in the height direction, like the cable group running space 150 illustrated, and thus the height of the microscope unit 5303 and the first rotation axis unit 5311a, or in other words the height of the microscope unit as a whole, can be shortened. Consequently, according to the present embodiment, it becomes possible to secure adequate space for the cable group 116 to move in association with rotation about the first axis $O_1$, while also further shortening the height of the microscope unit 5303 and the first rotation axis unit 5311a (that is, the microscope unit 5303 as a whole), and ensuring the surgeon's field of view.

Note that the installed number, installed position, and shape (particularly the cross-sectional area in the horizontal plane and the like) of the connecting member 124 are set so as not to impeded the movement of the cable group 116 in association with rotation about the first axis $O_1$. In the illustrated example, two connecting members 124 are provided at positions that hold the cable group entry position in between in the horizontal plane. As illustrated in FIGS. 3 and 4, when the microscope unit 5303 rotates about the first axis $O_1$, the cable group 116 is bent as the cable group entry position rotates about the first axis $O_1$ while the cable group exit position remains stationary. Consequently, as illustrated in the diagrams, by installing the connecting member 124 near the cable group entry position, when the cable group 116 moves inside the cable group running space 150 in association with the rotation of the microscope unit 5303 about the first axis $O_1$, a situation in which the cable group 116 interferes with the connecting member 124 is prevented.

At this point, the situation with the highest probability of the bent cable group 116 and the connecting member 124 touching is considered to be the case in which the cable group 116 is maximally bent (in other words, the case in which the microscope unit 5303 is rotated about the first axis $O_1$ to the limit of the movable range). In other words, to favorably prevent the cable group 116 from interfering with the connecting member 124 when the cable group 116 moves in association with the rotation of the microscope unit 5303 about the first axis $O_1$, it is sufficient to configure the connecting member 124 so that when the cable group 116 is maximally bent, the bent cable group 116 and the connecting member 124 do not touch. Specifically, it is preferable to configure the connecting member 124 so that the cross-sectional area in the horizontal plane is less than the area of the region enclosed by the bent cable group 116 (the shaded region X illustrated in FIG. 4) on the top face of the first member 121 when the cable group 116 is maximally bent.

The above thus describes the configuration of the microscope unit 5303 and the first rotation axis unit 5311a.

Herein, as the cross-sectional area of the cable group 116 becomes larger, the cable group 116 bends less easily. In other words, since the radius of curvature of the cable group 116 increases when bent, the size in the horizontal direction of the cable group running space 150 which is demanded to accommodate the bent cable group 116 becomes larger. In such a situation, the microscope unit 5303 as a whole becomes bulkier in the horizontal direction, which is not preferable. Consequently, in the present embodiment, to make the microscope unit 5303 more compact, the cross-sectional area of the cable group 116 preferably is smaller. For this reason, components with a narrow diameter may be used favorably as the signal cables 113 and the light guides 115. For example, thin-line coaxial cables may be used favorably as the signal cables 113.

Note that the signal cables 113 may be cables that transmit electrical signals, or cables that transmit optical signals. In the case in which optical signals are transmitted, the image sensor 112 is provided with a photoelectric transducer, and electrical signals may be converted into optical signals by such a photoelectric transducer and transmitted via the signal cables 113. Any of various known types of components can be used as the signal cables 113 and the light guides 115, insofar as the components enable the transmission of signals with desired characteristics and the guiding of light with desired characteristics. However, as described above, in order to make the cross-sectional area of the cable group 116 smaller, it is preferable to select components with as narrow a diameter as possible for the signal cables 113 and the light guides 115.

Herein, for example, as indicated in JP 2016-59499A, a method of running the signal cable in the up-and-down direction along the first axis $O_1$ has been disclosed as an existing method of running a signal cable inside the housing of a microscope unit and a first rotation axis unit in an electronic imaging observation device. According to such a configuration, since the signal cable operates so as to twist in association with the rotation of the microscope unit, the signal cable does not move greatly, and thus it is not necessary to secure a large space for the movement of the signal cable inside the housing of the microscope unit and the first rotation axis unit, thus contributing to the compactness of the microscope unit as a whole.

However, in JP 2016-59499A, a light guide is not considered. Typically, a light guide has a thicker diameter than a signal cable, and thus a cable group bundling a signal cable and a light guide has a large cross-sectional area. Consequently, if such a cable group is run in the up-and-down direction along the first axis $O_1$ as in the case of a signal cable only, when the cable group is twisted in association with rotation about the first axis $O_1$, a long space in the up-and-down direction becomes necessary to absorb twists. In other words, if the cable running method described in JP 2016-59499A is applied to a cable group including comparatively thick members such as a light guide, the height of the microscope unit and the first rotation axis unit becomes long, and making the microscope unit as a whole more compact becomes difficult.

In contrast, according to the present embodiment, by running the cable group 116 in the horizontal direction as described above, even in the case in which the cable group 116 includes thick members, the height of the microscope unit 5303 and the first rotation axis unit 5311a can be made shorter while still securing movement space for the cable group 116.

Note that the configuration illustrated in FIGS. 2 to 4 is merely one example, and the present embodiment is not limited to such an example. In the present embodiment, it is sufficient to provide, inside the housing of the microscope unit 5303 and the first rotation axis unit 5311a, the cable group running space 150 in which the cable group 116 is run in the horizontal direction, and the rest of the configuration may be arbitrary. If the cable group 116 is run in the horizontal direction inside the housing of the microscope unit 5303 and the first rotation axis unit 5311a, it is possible to obtain the above-described advantageous effect of shortening the height of the microscope unit 5303 and the first rotation axis unit 5311a further while still securing adequate space for the movement of the cable group 116.

For example, the part where the first bundling member 141 is provided may also not be a part on the outer circumference of the first member 121 of the first rotation member 120 as described above. In other words, in the illustrated example, the cable group entry position is a position which faces opposite the cable group exit position with the first axis $O_1$ interposed in between, and which corresponds to a part on the outer circumference in the horizontal direction of the cable group running space 150, but the present embodiment is not limited to such an example. The cable group entry position may be set arbitrarily. For example, the cable group entry position may be an arbitrary position on the outer circumference of the cable group running space 150 other than a position facing opposite the cable group exit position with the first axis $O_1$ interposed in between. As another example, the cable group entry position may also not be provided on the outer circumference of the cable group running space 150. In this case, for example, a penetrating hole is provided in the up-and-down direction in the first member 121, and the cable group 116 is inserted through this penetrating hole from below to enter the cable group running space 150 (in other words, the penetrating hole corresponds to the cable group entry position). In this case, the first bundling member 141 may be provided directly below the penetrating hole to bundle the cable group 116. However, in this case, if the cable group entry position and the first axis $O_1$ are aligned, the configuration becomes similar to the configuration described in JP 2016-59499A. Consequently, in the present embodiment, the cable group entry position may be set arbitrarily, but a position aligned with the first axis $O_1$ should be avoided.

However, in the present embodiment, the distance in the horizontal direction from the cable group entry position to the cable group exist position in the cable group running space 150 corresponds to an effective distance for absorbing the movement of the cable group 116 in association with rotation about the first axis $O_1$. Consequently, to absorb the movement of the cable group 116 more favorably, a longer distance in the horizontal direction from the cable group entry position to the cable group exist position is preferable. Consequently, to make the distance longer, the cable group entry position is provided more preferably at a position which faces opposite the cable group exit position with the first axis $O_1$ interposed in between, and which corresponds to a part on the outer circumference in the horizontal direction of the cable group running space 150, like the exemplary configuration described above.

Also, the installed number, installed position, and shape of the connecting member 124 are not limited to the illustrated example. As described above, the specific configuration of the connecting member 124 may be arbitrary, insofar as the installed number, installed position, and shape are set so as not to impede the movement of the cable group 116 in association with rotation about the first axis $O_1$. However, as described above, to favorably prevent interference between the connecting member 124 and the cable group 116, the connecting member 124 more preferably is installed at a position near the cable group entry position, like the exemplary configuration described above.

(3. Operation During Use)

Operation during the use of the observation device 10 according to the present embodiment will be described. First, as a preparation before use (before surgery), to ensure the hygiene of the holding unit 5309, the holding unit 5309 is covered with a sterilized drape.

Next, a medical staff member uses the casters of the base unit 5315 to move the observation device 10 close to an operating table on which a patient is lying.

Next, the surgeon grasps a grip part of the microscope unit 5303 through the sterilized drape, and while pushing the operating mode toggle switch to set the operating mode of the holding unit 5309 to the free mode (in other words, while releasing the brakes provided on the first axis $O_1$ to the sixth axis $O_6$), adjusts the position and the attitude of the microscope unit 5303 so that the operative site may be imaged from a desired direction and a desired angle of view. At this point, the surgeon also adjusts the facing the microscope unit 5303, or in other words the rotational angle of the microscope unit 5303 about the first axis $O_1$, so that the surgeon is face-to-face with the operative site. As described above, in the present embodiment, since the cable group running space 150 is sufficiently secured inside the housing of the microscope unit 5303 and the first rotation axis unit 5311a, a situation in which the movement of the cable group 116 hinders such rotation of the microscope unit 5303 about the first axis $O_1$ is prevented.

After the adjustment of the position and the attitude of the microscope unit 5303 is finished, the surgeon releases the above toggle switch, and changes the operating mode of the holding unit 5309 to the locked mode (in other words, causes the brakes provided on the first axis $O_1$ to the sixth axis $O_6$ to operate). Subsequently, the surgeon starts the surgery while referring to the display device 20 depicting a picture of the operative site imaged by the microscope unit 5303. At this point, according to the present embodiment, since the cable group 116 is run through the cable group running space 150 in the horizontal direction, the microscope unit 5303 and the first rotation axis unit 5311a may be configured with a shorter height. Consequently, it becomes possible to ensure more favorably the field of view of the surgeon viewing the display device 20.

(4. Modifications)

Several modifications of the configuration of the microscope unit 5303 and the first rotation axis unit 5311*a* described above will be described.

(4-1. Modification Provided with Partitioning Plate)

Figure 5:
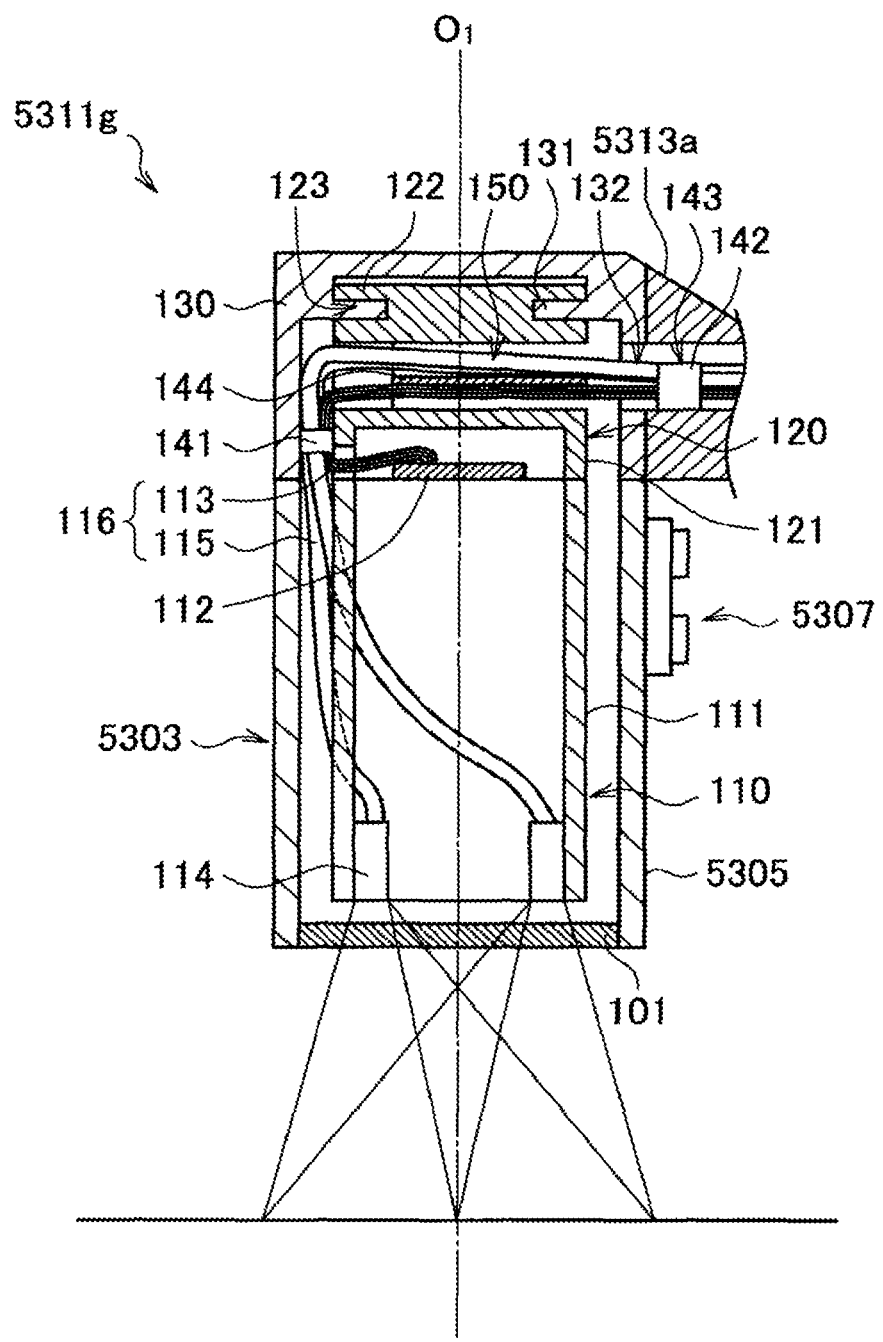
FIG. 5 is a cross section diagram that schematically illustrates a configuration around a microscope unit and a first rotation axis unit according to a modification provided with a partitioning plate.

A configuration of the microscope unit 5303 and a first rotation axis unit 5311*g* according to a modification provided with a partitioning plate will be described with reference to FIG. 5. FIG. 5 is a cross section diagram that schematically illustrates the configuration around the microscope unit 5303 and the first rotation axis unit 5311*g* according to the modification provided with a partitioning plate. FIG. 5 illustrates a cross section, taken along the optical axis, of the configuration around the microscope unit 5303 and the first rotation axis unit 5311*g*. Note that the configuration of the microscope unit 5303 and the first rotation axis unit 5311*g* according to the present modification is similar to the configuration of the microscope unit 5303 and the first rotation axis unit 5311*a* according to the embodiment described earlier, except that a partitioning plate 144 described later is provided in the cable group running space 150. Consequently, in the following, description of items shared in common with the embodiment described earlier will be reduced or omitted.

As illustrated in FIG. 5, in the present modification, in the cable group running space 150, there is provided a partitioning plate 144 extending in the horizontal direction that divides the cable group running space 150 into two spaces in the up-and-down direction. Additionally, when the cable group 116 is run through the cable group running space 150, the signal cables 113 and the light guides 115 are run through respective spaces that are mutually different and formed due to the separation by the partitioning plate 144.

According to such a configuration, when the cable group 116 moves (bends) in the cable group running space 150 in association with the rotation of the microscope unit 5303 about the first axis $O_1$, the signal cables 113 and the light guides 115 bend inside respective different spaces. Herein, in the embodiment described earlier, the signal cables 113 and the light guides 115 are bent together in a bundled state in the same space, and thus the two may interfere with each other. However, since the signal cables 113 and the light guides 115 have different diameters as described earlier, the radius of curvature when bent may also be different. Specifically, the thinner signal cables 113 have a small radius of curvature, while the thicker light guides 115 have a large radius of curvature. Consequently, for example, in a case in which the light guides 115 are pulled tight by the bending signal cables 113, there is a risk of the light guides 115 being bent excessively, up to a radius of curvature that is smaller than the original, comparatively large radius of curvature. Excessive bending of the light guides 115 in this way may lead to damage to the light guides 115.

In contrast, according to the present modification, by providing the partitioning plate 144, the signal cables 113 and the light guides 115 are run through respective different spaces. Consequently, interference between the signal cables 113 and the light guides 115 when bending as above is prevented. Thus, a situation in which the light guides 115 are bent excessively can be avoided, and damage to the light guides 115 may also be prevented. Thus, a more reliable observation device 10 may be provided.

(4-2. Another Exemplary Configuration of Cable Group Running Space)

A modification in which the cable group running space is formed by a different method from the embodiment described earlier will be described with reference to FIG. 6.

Figure 6:
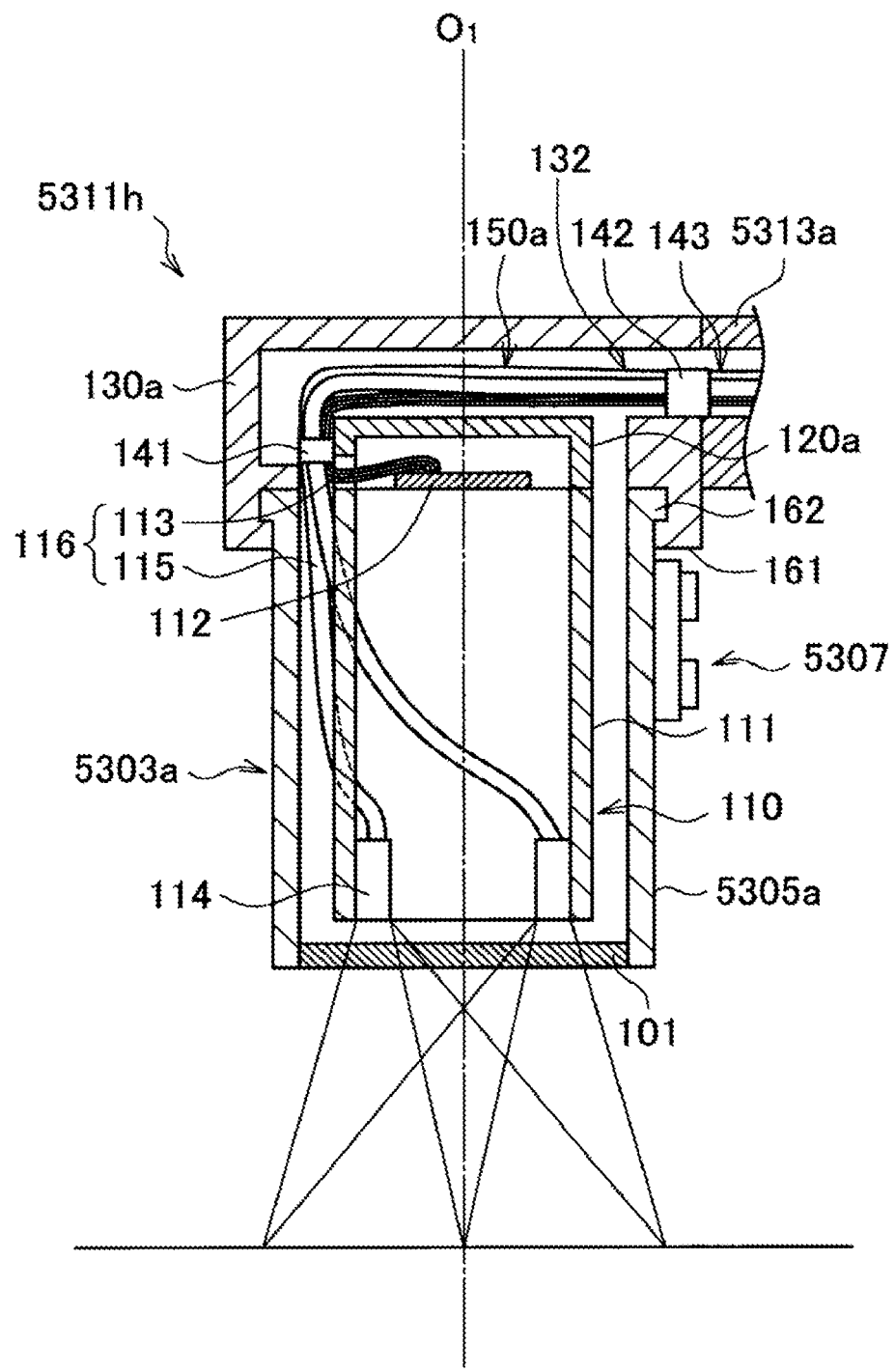
FIG. 6 is a cross section diagram that schematically illustrates a configuration around a microscope unit and a first rotation axis unit according to a modification in which a cable group running space is formed by a different method.

FIG. 6 is a cross section diagram that schematically illustrates a configuration around a microscope unit 5303*a* and a first rotation axis unit 5311*h* according to a modification in which the cable group running space is formed by a different method. FIG. 6 illustrates a cross section, taken along the optical axis, of the configuration around the microscope unit 5303*a* and the first rotation axis unit 5311*h*. Note that in the present modification, the configuration of the microscope unit 5303*a* is similar to the embodiment described earlier, except that an engaging part 162 described later is provided on a barrel unit 5305*a*. Thus, herein, the description of duplicate items will be reduced or omitted.

Referring to FIG. 6, the first rotation axis unit 5311*h* includes a first rotation member 120*a* which is disposed on the top end (base end) of the imaging unit 110 and which securely supports the imaging unit 110 (in other words, disposed on the base end of the microscope unit 5303*a*, and securely supports the microscope unit 5303*a*), and a second rotation member 130*a* which is disposed to cover the first rotation member 120*a* and which supports the barrel unit 5305*a* of the microscope unit 5303*a* to allow rotation about the first axis $O_1$. In other words, when the microscope unit 5303*a* rotates about the first axis $O_1$, the first rotation member 120*a*, the imaging unit 110, and the barrel unit 5305*a* also rotate in a state of being supported by the second rotation member 130*a*.

The first rotation member 120*a* has a substantially hollow round cylindrical shape with a floor on one end, and of substantially equal diameter to the housing 111 of the imaging unit 110. The first rotation member 120*a* is disposed on the top part of the housing 111 so that the open part faces downward and the floored part faces upward. In other words, the first rotation member 120*a* is disposed to cover the top of the imaging unit 110. The first rotation member 120*a* is securely connected to the top end of the housing 111.

The second rotation member 130*a* has a substantially hollow round cylindrical shape with a floor on one end. The second rotation member 130*a* is disposed on the top part of the barrel unit 5305*a* so that the open part faces downward and the floored part faces upward. In other words, the second rotation member 130*a* is disposed to cover the outer circumference and top of the first rotation member 120*a*.

The second rotation member 130*a* is configured so that the inner diameter is larger than the outer diameter of the barrel unit 5305*a*, and the bottom end of the opening reaches below the top end of the barrel unit 5305*a*. The perimeter of the opening of the second rotation member 130*a* is provided with a flange part 161 that projects inward in the radial direction. Meanwhile, in the present modification, an engaging part 162 that projects outward in the radial direction is provided on the top end of the barrel unit 5305*a*. Additionally, by having the engaging part 162 of the barrel unit 5305*a* engage with the flange part 161 of the second rotation member 130*a*, the second rotation member 130*a* is connected to the barrel unit 5305*a*. At this point, the two are not connected securely, with the barrel unit 5305*a* in a state of being supported by the second rotation member 130*a* while allowing rotation about the first axis $O_1$.

In the configuration according to the present modification, the cable group 116 is run in the horizontal direction in the space between the top face of the first rotation member 120*a* and the bottom face of the floored part of the second rotation member 130*a*. In other words, this space functions as a cable group running space 150*a*. In this way, in the embodiment described earlier, the cable group running space 150 is formed inside the first rotation member 120, but in the present modification, the cable group running space 150*a* is formed between the first rotation member 120a and the second rotation member 130a. Even with the configuration according to the present modification, by running the cable group 116 in the horizontal direction in the cable group running space 150a, it is possible to obtain advantageous effects similar to the embodiment described earlier.

The above thus describes a modification in which the cable group running space 150a is formed by a different method. As described above, the present modification corresponds to a modification of the embodiment described earlier, in which the member that is rotatably supported by the second rotation member 130a has been changed, and in which the part where the cable group running space 150a is formed has been changed.

Specifically, in the embodiment described earlier, the second rotation member 130 rotatably supports the first rotation member 120, as illustrated in FIG. 2. With such a configuration, it is necessary to provide a configuration by which the second rotation member 130 supports the first rotation member 120 and also provides the cable group running space 150 above the imaging unit 110. Consequently, the first rotation member 120 is divided into two members in the up-and-down direction (namely, the first member 121 and the second member 122), and the second member 122 provided higher up is supported by the second rotation member 130, while in addition, the cable group running space 150 is formed between the first member 121 and the second member 122.

Meanwhile, when the microscope unit 5303 rotates about the first axis $O_1$, the first rotation member 120, the imaging unit 110, and the barrel unit 5305 also rotate in a state of being supported by the second rotation member 130, and thus it is sufficient for the second rotation member 130 to rotatably support at least one of the first rotation member 120, the imaging unit 110, and the barrel unit 5305. Accordingly, in the present modification, the barrel unit 5305a is rotatably supported by the second rotation member 130a, as illustrated in FIG. 6. With such a configuration, it is not necessary to provide a configuration by which the second rotation member 130a supports the first rotation member 120a, and it is sufficient to provide only the cable group running space 150a. Consequently, since it is not necessary to form on the first rotation member 120a a part supported by the second rotation member 130a, the first rotation member 120a can be configured with one member rather than two members.

In other words, in the configuration according to the embodiment described earlier, the configuration by which the second rotation member 130 supports the first rotation member 120 and the cable group running space 150 are both provided above the imaging unit 110, and thus the configuration of the first rotation member 120 becomes complicated, while in addition, there are concerns that the height of the first rotation member 120 becomes comparatively high. In contrast, with the configuration according to the present modification, since it is not necessary to provide a part by which the second rotation member 130a supports the first rotation member 120a above the imaging unit 110, and it is sufficient to provide only the cable group running space 150a, the first rotation member 120a can be configured more simply and with a lower height. As a result, according to the present modification, the height of the microscope unit 5303a and the first rotation axis unit 5311h (that is, the microscope unit 5303a as a whole) can be made shorter than the embodiment described earlier, thus further contributing to the securing of the surgeon's field of view.

(5. Method of Running Cable Group in Other Parts of Holding Unit)

The above thus describes a method of running the cable group 116 inside the housing of the microscope unit 5303 and the first rotation axis unit 5311a. Herein, as described above, in the present embodiment, the cable group 116 is run from the microscope unit 5303, along the holding unit 5309, to the base end of the holding unit 5309. At this point, the cable group 116 is also run through each rotation axis unit, but in each rotation axis unit, the cable group 116 may be twisted in association with the rotation. If the cable group 116 is twisted, a torsion load is imparted to the twisted cable group 116. If the torsion load is large, the danger of damage to the cable group 116 increases. Also, since a reaction force working to revert the cable to normal acts on the cable group 116 subjected to the torsion load, there is a risk of each rotation axis unit no longer rotating smoothly due to the reaction force. Consequently, to order to avoid these situations, in each rotation axis unit, it is preferable to further minimize the torsion load subjected to the cable group 116 in association with the rotation of each rotation axis unit.

Accordingly, in the present embodiment, to further decrease the torsion load subjected to the cable group 116 in association with rotation, innovations may be made to the method of running the cable group 116 in each rotation axis unit other than the first rotation axis unit 5311a in the holding unit 5309. Herein, a preferable method of running the cable group 116 in a rotation axis unit other than the first rotation axis unit 5311a will be described.

As an example, a method of running the cable group 116 in the third rotation axis unit 5311c will be described. However, it is possible to obtain similar advantageous effects by taking a similar configuration in the other rotation axis units.

Figure 7:
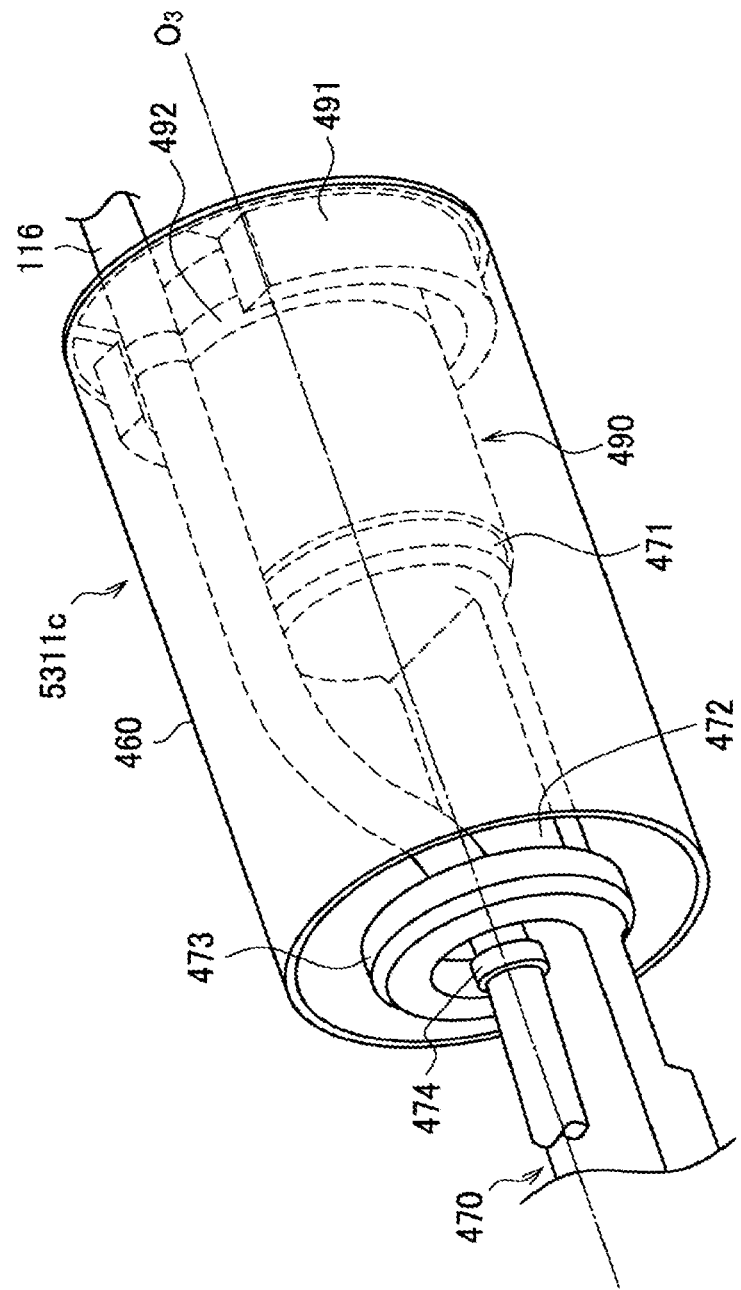
FIG. 7 is a diagram illustrating an extraction of the configuration near the third rotation axis unit illustrated in FIG. 1.
Figure 8:
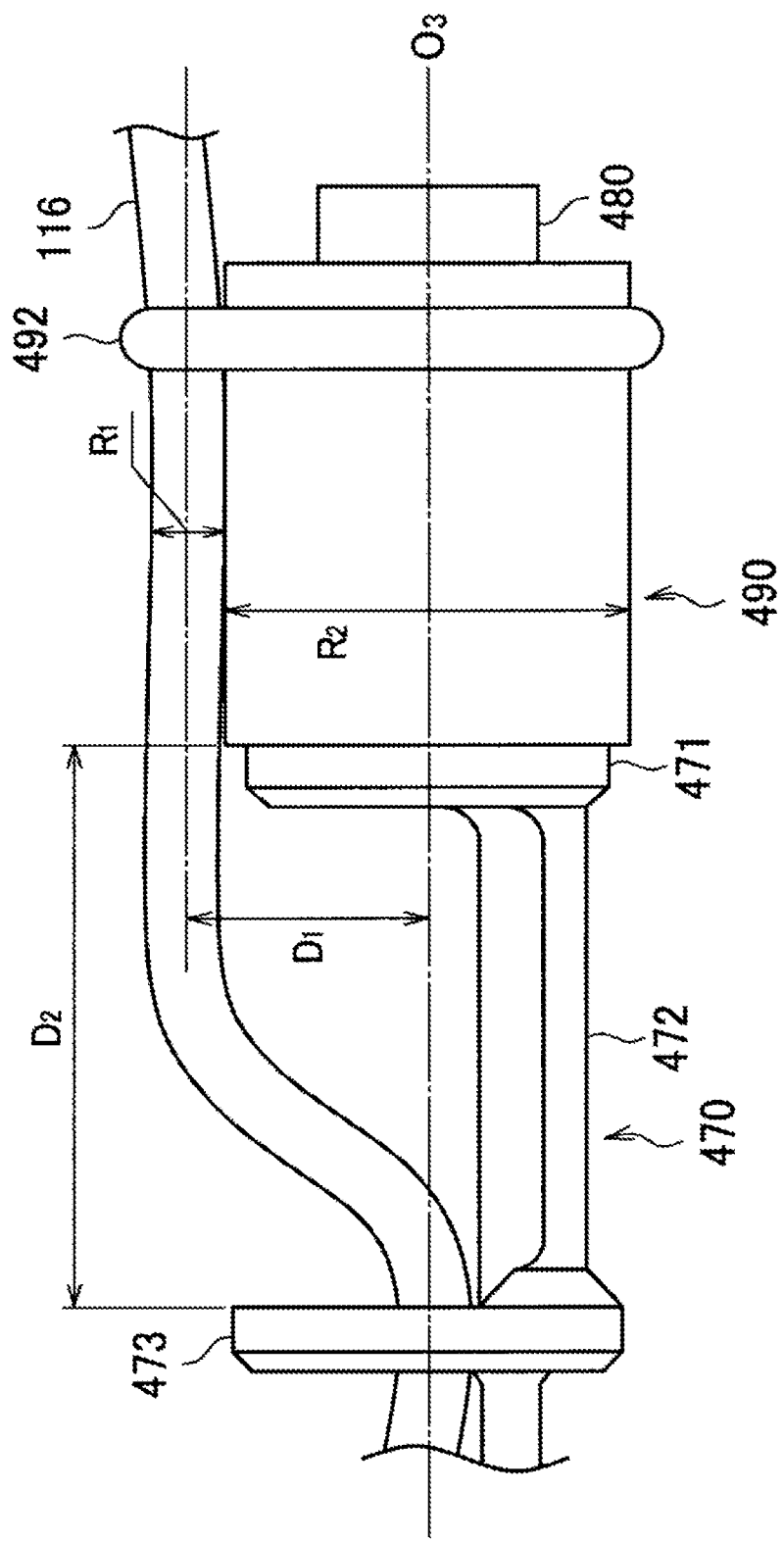
FIG. 8 is a diagram illustrating an extraction of the configuration near the third rotation axis unit illustrated in FIG. 1.
Figure 9:
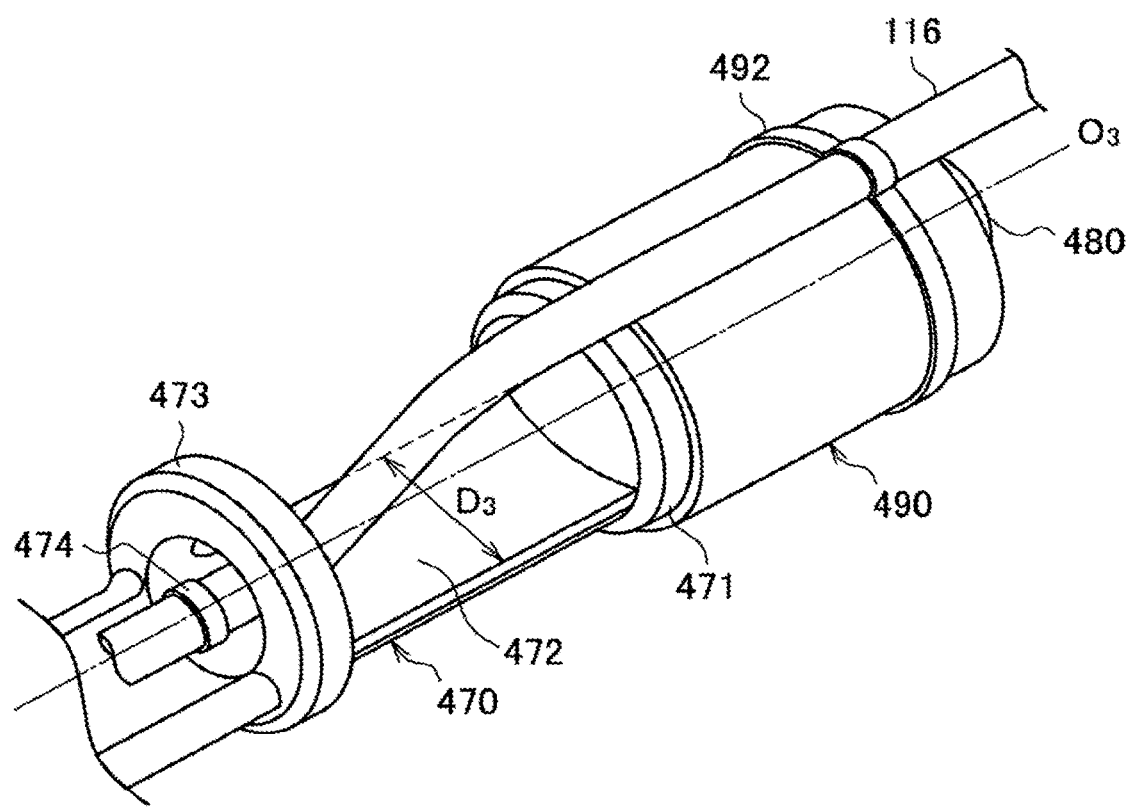
FIG. 9 is a diagram illustrating an extraction of the configuration near the third rotation axis unit illustrated in FIG. 1.
Figure 10:
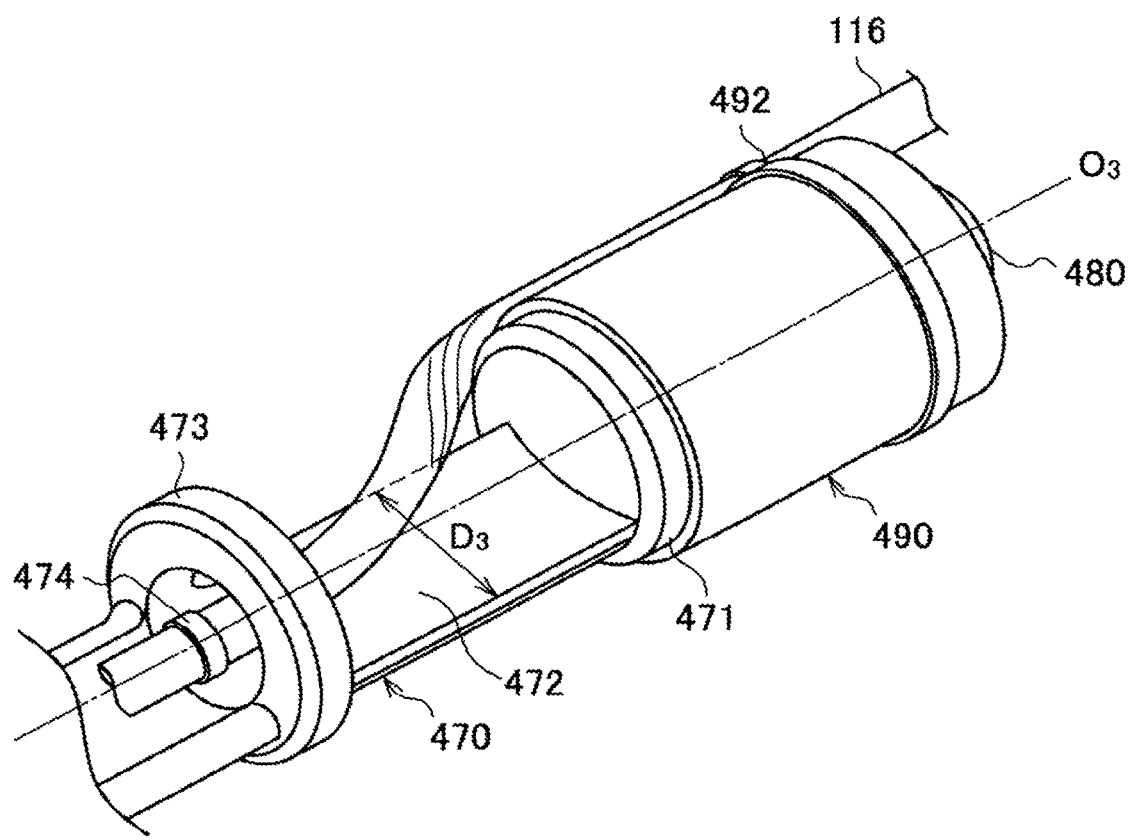
FIG. 10 is a diagram illustrating an extraction of the configuration near the third rotation axis unit illustrated in FIG. 1.

FIGS. 7 to 10 are diagrams illustrating an extraction of the configuration near the third rotation axis unit 5311c illustrated in FIG. 1. FIG. 7 is a perspective diagram of the third rotation axis unit 5311c, while FIG. 8 is a side view illustrating a state in which a cover 460 and a joining member 491 described later have been removed from the third rotation axis unit 5311c, and FIG. 9 is a perspective diagram illustrating a state in which the cover 460 and the joining member 491 described later have been removed from the third rotation axis unit 5311c. FIG. 10 is a perspective diagram illustrating a state in which the third rotation axis unit 5311c has rotated about the third axis $O_3$ from the state illustrated in FIG. 9. Note that in FIGS. 7 to 10, for the sake of simplicity, the cable group 116 is illustrated as a single cable. In actuality, as described earlier, the cable group 116 is a bundle of multiple signal cables 113 and multiple light guides 115.

Herein, FIGS. 7 to 9 illustrate states in which the cable group 116 is not twisted, and a torsion load is not being imparted to the cable group 116. Herein, a state in which a torsion load is not being imparted refers to a state in which the central axis of the cable group 116 (the axis passing through the center of gravity in a cross section of the cable group 116) is on the plane that passes through the rotation axis of the third rotation axis unit 5311c (third axis $O_3$). In the present embodiment, the third rotation axis unit 5311c is configured so that the central axis of the cable group 116 is positioned on the plane that passes through the third axis $O_3$ in a state in which the third rotation axis unit 5311c is not rotating, or in other words, in the case in which the rotational angle of the third rotation axis unit 5311c is zero. Thus, the state in which a torsion load is not being imparted may mean a state in which the rotational angle of the third rotation axis unit 5311*c* is zero. On the other hand, FIG. 10 illustrates a state in which the third rotation axis unit 5311*c* has rotated about the third axis O₃ from the state illustrated in FIG. 9 as described above. In other words, FIG. 10 illustrates a state in which the cable group 116 is twisted, and a torsion load is being imparted to the cable group 116.

Referring to FIGS. 7 to 9, the third rotation axis unit 5311*c* includes a cover 460 which has a tubular shape and which is connected to the second arm unit 5313*b* illustrated in FIG. 1 on the front end side, an extending part 470 that extends towards the third arm unit 5313*c* illustrated in FIG. 1, a rotation axis part 480 which is provided on the end on the opposite side of the side where the extending part 470 is connected to the third arm unit 5313*c* and whose central axis is aligned with the third axis O₃, and a rotating part 490 which is rotatable about the rotation axis part 480.

The extending part 470 includes a disc-shaped fixed part 471 that is affixed to the rotation axis part 480, a planar joining part 472 which is joined to the fixed part 471 and which connects the fixed part 471 and the third arm unit 5313*c*, and a guide part 473 which forms a C-shape and whose open end is affixed to the joining part 472, and which forms a midair space through which the cable group 116 can be inserted and guided. The joining part 472 extends to form a planar shape along the third axis O₃, and the third arm unit 5313*c* is connected on the front end.

The rotating part 490 is configured to be rotatable about the rotation axis part 480. The rotating part 490 is joined to the inner circumferential part of the cover 460 by the joining member 491. For this reason, if the rotating part 490 rotates about the rotation axis part 480, the cover 460 rotates in conjunction with the rotation of the rotating part 490. If the cover 460 rotates, the second arm unit 5313*b* joined to the cover 460 rotates about the rotation axis part 480, or in other words, the third axis O₃.

In the third rotation axis unit 5311*c*, the cable group 116 is affixed to the joining part 472 and the rotating part 490 by bundling members 474 and 492, respectively. Specifically, the bundling member 474 affixes the cable group 116 to the joining part 472 in the midair space of the guide part 473. At the affixing location provided by the bundling member 474, the central axis of the cable group 116 is substantially aligned with the third axis O₃. Meanwhile, the bundling member 492 affixes the cable group 116 to the rotating part 490 at a part on the outer circumference of the rotating part 490. The affixed positions of the cable group 116 provided by the bundling members 474 and 492 preferably are provided respectively on one end and the other end of the third rotation axis unit 5311*c* in the direction of the third axis O₃.

By affixing the cable group 116 in this way, the affixed location of the cable group 116 on the joining part 472 and the affixed location of the cable group 116 on the rotating part 490 enter an offset state as viewed from the direction of the third axis O₃. Specifically, at the affixed location of the cable group 116 on the joining part 472, the central axis of the cable group 116 is substantially aligned with the third axis O₃, but at the affixed location of the cable group 116 on the rotating part 490, the central axis of the cable group 116 is away from the third axis O₃ by a predetermined distance (a distance corresponding to the outer diameter of the rotating part 490). Note that a state in which a first part and another part in the extension direction of the cable group 116 are offset refers to a state in which the central axis of the cable group 116 in the first part and the central axis of the cable group 116 in the other part are not positioned on substantially the same line.

In this way, by making the central axis of the cable group 116 at the joining part 472 substantially aligned with the third axis O₃, and placing the central axis of the cable group 116 on the rotating part 490 away from the third axis O₃, the torsion load imposed on the cable group 116 due to the rotation of the rotating part 490 can be decreased compared to the torsion load imposed in the case in which the central axis of the cable group 116 on the rotating part 490 is substantially aligned with the third axis O₃. This is because the cable group 116 is twisted by a smaller amount in the case in which the rotating part 490 rotates while the central axis of the cable group 116 is away from the third axis O₃ by a predetermined distance, compared to the case in which the rotating part 490 rotates while the central axis of the cable group 116 is substantially aligned with the third axis O₃.

Note that, provided that $R_1$ is the diameter of the cable group 116, $R_2$ is the outer circumference of the rotating part 490, and $D_1$ is the distance between the third axis O₃ and the center of the cable group 116, the diameter $R_1$, the diameter $R_2$, and the distance $D_1$ preferably satisfy the relationship $D_1 = \frac{1}{2} \times R_1 + \frac{1}{2} \times R_2$. Also, the diameter $R_1$ and the distance $D_1$ preferably satisfy the relationship $2 \times R_1 \leq D_1$. As a result of investigation by the inventors, in a case in which at least one of these relationships is satisfied, the torsion load imposed on the cable group 116 due to the rotation of the rotating part 490 can be decreased favorably.

Also, provided that $D_3$ is the width the joining part 472 and the width in the direction orthogonal to the third axis O₃ in the principal plane, the diameter $R_2$ and the width $D_3$ preferably satisfy the relationship $D_3 < R_2$. Herein, the principal plane refers to the plane having the greatest area of the joining part 472. By satisfying this relationship, interference between the cable group 116 and the joining part 472 when the rotating part 490 rotates can be decreased, making it possible for the rotating part 490 to rotate more smoothly. Also, if the width $D_3$ is increased while satisfying the above relationship, the joining between the rotation axis part 480 and the third arm unit 5313*c* can be made stronger.

In addition, provided that $D_2$ is the distance in the direction of the third axis O₃ from the end of the extending part 470 on the rotating part 490 side to the affixed location of the cable group 116 provided by the bundling member 474, a larger distance $D_2$ is preferable from the perspective of reducing the torsion load. As illustrated in FIG. 10, if the rotating part 490 is rotated, the cable group 116 is wound around the joining part 472. By having the cable group 116 wind around the joining part 472, the twisting of the cable group 116 about the central axis of the cable group 116 itself can be minimized, and the torsion load can be decreased. As the distance $D_2$ becomes larger, the distance over which the cable group 116 winds around the joining part 472 becomes longer, thereby making it possible to decrease the torsion load favorably. Note that although FIG. 10 illustrates a case in which the rotating part 490 is rotated in one direction from a reference position at which the rotational angle is zero, the case in which the rotating part 490 is rotated in the opposite direction with respect to the reference position is also similar.

The above thus describes an example of running the cable group 116 in each rotation axis unit other than the first rotation axis unit 5311*a*. As described above, for the third rotation axis unit 5311*c*, the central axis of the cable group 116 at the joining part 472, which is the part on the base end side that does not rotate relatively, is substantially aligned with the third axis O₃, while the central axis of the cable group 116 at the rotating part 490, which is the part on the front end side that rotates relatively, is placed away from the third axis $O_3$. With this arrangement, the torsion load imposed on the cable group 116 by the rotation of the rotating part 490 (that is, the rotation of the third rotation axis unit 5311c) can be decreased further. Consequently, damage to the cable group 116 due to the torsion load can be moderated. Additionally, since the reaction force due to the torsion load is also kept low, the third rotation axis unit 5311c can be rotated more smoothly, and operability can be improved.

Herein, in the exemplary configuration described above, the amount of twisting of the cable group 116 about the central axis in association with the rotation of the third rotation axis unit 5311c can be reduced compared to the case in which the central axis of the cable group 116 on the rotating part 490 is substantially aligned with the third axis $O_3$, but the amounts of spatial movement and deformation of the cable group 116 become larger. Meanwhile, as described earlier, the cable group 116 is a bundle of multiple signal cables 113 and multiple light guides 115. Consequently, in the exemplary configuration described above, as the third rotation axis unit 5311c is rotated repeatedly, and the cable group 116 repeatedly undergoes operations of moving while rotating together with the rotating part 490, there are concerns of a situation occurring in which the multiple signal cables 113 and the multiple light guides 115 become entangled. If the signal cables 113 and the light guides 115 become entangled, there is a danger of the two being damaged, and thus such a situation is not considered preferable.

Figure 11:
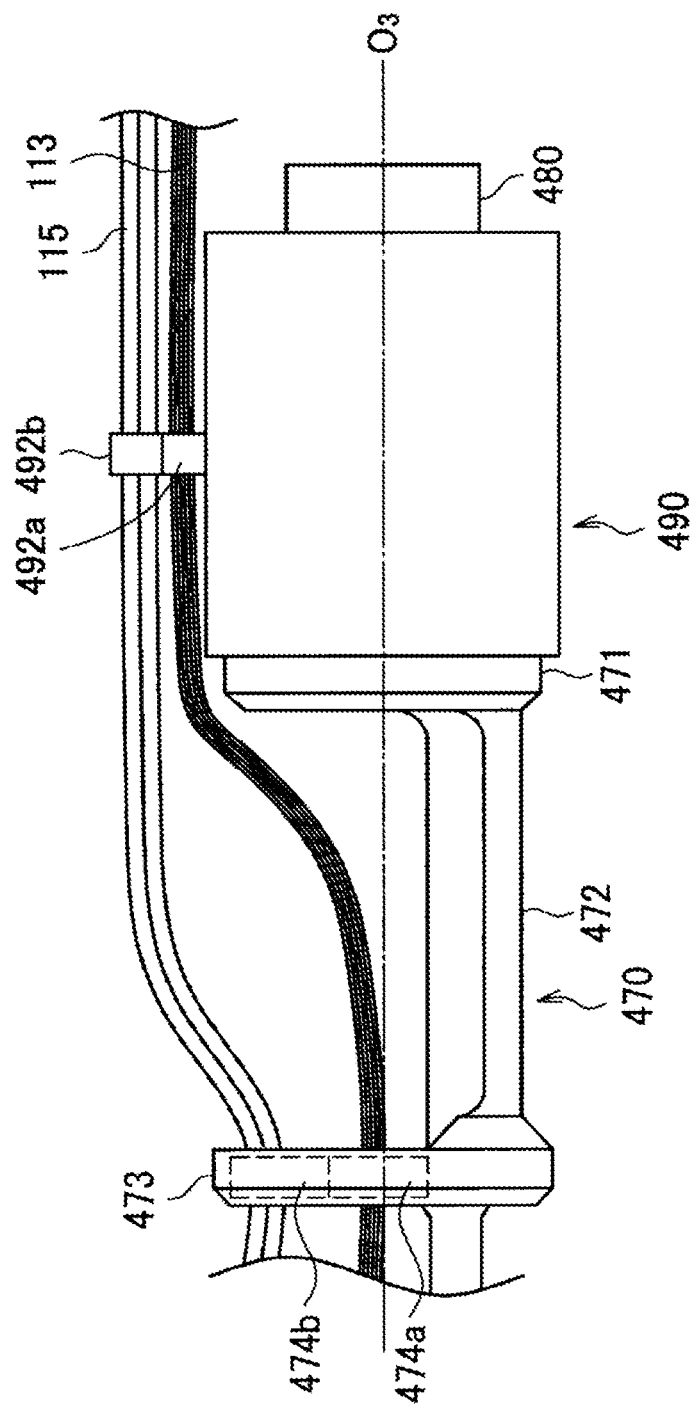
FIG. 11 is a diagram illustrating another example of a method of running a cable group in a third rotation axis unit.

Accordingly, as another example of a method of running the cable group 116 in a rotation axis unit, a configuration as illustrated in FIG. 11 may also be adopted. FIG. 11 is a diagram illustrating another example of a method of running the cable group 116 in the third rotation axis unit 5311c. Similarly to FIG. 8, FIG. 11 is a diagram illustrating an extraction of the configuration near the third rotation axis unit 5311c from the holding unit 5309, and is a side view illustrating a state in which the cover 460 and the joining member 491 have been removed from the third rotation axis unit 5311c.

In the exemplary configuration illustrated in FIG. 11, the cable group 116 is bundled into the signal cables 113 and the light guides 115. Additionally, the affixing of the cable group 116 on the outer circumference of the joining part 472 and the rotating part 490 is performed respectively for the signal cables 113 and the light guides 115. Specifically, on the joining part 472, a bunch of the signal cables 113 is bundled by a bundling member 474a, while a bunch of the light guides 115 is bundled by the bundling member 474b. At this time, the bundling member 474a and the bundling member 474b are arranged by being stacked in the direction in which the cable group 116 (that is, the signal cables 113 and the light guides 115) are arranged away from the third axis $O_3$ on the rotating part 490 (the vertical direction on the page). In other words, the bunch of the signal cables 113 and the bunch of the light guides 115 are arranged stacked on top of each other. In the illustrated example, the bunch of the signal cables 113 is positioned lower on the page, or in other words on the side closer to the third axis $O_3$, while the bunch of the light guides 115 is arranged stacked on top, but the positional relationship of the two may also be reversed.

Similarly, on the outer circumference of the rotating part 490, the bunch of the signal cables 113 and the bunch of the light guides 115 are affixed by bundling members 492a and 492b, respectively, in the state of being arranged stacked in the direction in which the cable group 116 (that is, the signal cables 113 and the light guides 115) is arranged away from the third axis $O_3$ on the rotating part 490 (the vertical direction on the page). In the illustrated example, in correspondence with the arrangement of the joining part 472, the bunch of the signal cables 113 is positioned lower on the page, or in other words on the side closer to the third axis $O_3$, while the bunch of the light guides 115 is arranged stacked on top, but if the stacking order of the two is reversed on the joining part 472, the stacking order of the two on the rotating part 490 is also reversed.

Furthermore, as illustrated in the diagram, between the two affixed locations, or in other words, between the joining part 472 and the rotating part 490, the bunch of the signal cables 113 arranged on the lower side at the affixed locations is run to curve downward (that is, to have slack), while the bunch of the light guides 115 arranged on the upper side at the affixed locations is run to curve upward.

According to such a configuration, since the bunch of the signal cables 113 and the bunch of the light guides 115 are affixed at positions away from the third axis $O_3$ on the rotating part 490, an advantageous effect of reducing the torsion load can be obtained similarly to the exemplary configuration described earlier in which the two are handled together as the cable group 116. Furthermore, according to the present exemplary configuration, the affixed locations of the bunch of the signal cables 113 and the bunch of the light guides 115 are separated, while in addition, the two are run away from each other between the two affixed locations. Thus, when the bunch of the signal cables 113 and the bunch of the light guides 115 rotate in association with the rotation of the rotating part 490, a situation in which the two become entangled may be minimized favorably. Thus, it becomes possible to reduce the torsion load produced in the signal cables 113 and the light guides 115, while also further minimizing a situation in which the two become entangled and damaged.

FIG. 11 illustrates another example of a method of running the cable group 116 in the third rotation axis unit 5311c as one example, but the method of running the cable group 116 illustrated in FIG. 11 may also be applied to other rotation axis units.

(6. Supplemental Remarks)

It should be understood by those skilled in the art that various modifications, combinations, sub-combinations and alterations may occur depending on design requirements and other factors insofar as they are within the scope of the appended claims or the equivalents thereof.

For example, in the above embodiment, the cable group 116 includes the signal cables 113 and the light guides 115, but the present technology is not limited to such an example. Any types of cables which are run from the microscope unit 5303 to the outside may also be included in the cable group 116.

Also, in the modification described in (4-1. Modification provided with partitioning plate) above, since the cable group 116 includes the two types of cables of the signal cables 113 and the light guides 115, the cable group running space 150 correspondingly is divided into two spaces. However, the present technology is not limited to such an example, and if more types of cables are included in the cable group 116, the number of spaces formed by dividing the cable group running space 150 may be increased correspondingly. In other words, multiple partitioning plates 144 may be provided as necessary and the cable group running space 150 may be divided as appropriate to form a number of spaces corresponding to the types of cables included in the cable group 116.

Further, the effects described in this specification are merely illustrative or exemplified effects, and are not limitative. That is, with or in the place of the above effects, the technology according to an embodiment of the present disclosure may achieve other effects that are clear to those skilled in the art from the description of this specification.

Additionally, the present technology may also be configured as below.

(1) A medical observation device including:
a microscope unit that includes an image sensor and images an operative site; and
a holding unit that holds the microscope unit on a front end side, in which
the holding unit includes a first rotation axis unit that supports the microscope unit to allow rotation about a first rotation axis substantially aligned with an optical axis of the microscope unit,
from the microscope unit, a cable group including at least a signal cable that transmits a signal related to the image sensor and a light guide that guides illuminating light for imaging is run towards an outside through an interior of a housing of the first rotation axis unit, and
the cable group is run, at a position that does not match the first rotation axis when facing from the microscope unit towards the interior of the housing of the first rotation axis unit, in a direction substantially parallel to the first rotation axis, and run in a direction substantially parallel to a plane that is orthogonal to the first rotation axis in the interior of the housing of the first rotation axis unit.

(2) The medical observation device according to (1), in which
the first rotation axis unit includes
a first rotation member that is connected to the microscope unit, and rotates together with the microscope unit about the first rotation axis, and
a second rotation member that supports the first rotation member to allow rotation about the first rotation axis on an opposite side from a side connected to the microscope unit, and
the cable group is run in the direction substantially parallel to the plane orthogonal to the first rotation axis inside the first rotation member.

(3) The medical observation device according to (2), in which
the first rotation member includes
a first member that is connected to the microscope unit and has a planar surface substantially orthogonal to the first rotation axis,
a second member that has a planar surface substantially orthogonal to the first rotation axis, and is disposed on an opposite side from a side of the first rotation member where the microscope unit is connected so that the planar surface has a predetermined interval with the planar surface of the first rotation member in a direction of the first rotation axis, and
a connecting member that connects the planar surface of the first member and the planar surface of the second member in the direction of the first rotation axis, and
the cable group is run in a direction substantially parallel to a plane orthogonal to the first rotation axis in a space between the planar surface of the first member and the planar surface of the second member.

(4) The medical observation device according to (3), in which
a cross-sectional area of the connecting member in the plane orthogonal to the first rotation axis is less than an area of a region on the planar surface of the first member, the region being enclosed by the cable group which curves when the microscope unit is rotated about the first rotation axis up to a limit of a movable range.

(5) The medical observation device according to (1), in which
the first rotation axis unit includes
a first rotation member that is connected to the microscope unit, and rotates together with the microscope unit about the first rotation axis, and
a second rotation member that supports the microscope unit to allow rotation about the first rotation axis,
the first rotation member has a planar surface substantially orthogonal to the first rotation axis,
the second rotation member has a planar surface substantially orthogonal to the first rotation axis, and is disposed on an opposite side from a side of the first rotation member where the microscope unit is connected so that the planar surface has a predetermined interval with the planar surface of the first rotation member in a direction of the first rotation axis, and
the cable group is run in a direction substantially parallel to a plane orthogonal to the first rotation axis in a space between the planar surface of the first rotation member and the planar surface of the second rotation member.

(6) The medical observation device according to any one of (1) to (5), in which
a partitioning plate is provided, the partitioning plate dividing a space in the interior of the housing of the first rotation axis unit through which the cable group is run in the direction substantially parallel to the plane orthogonal to the first rotation axis into at least two spaces in a direction parallel to the first rotation axis.

(7) The medical observation device according to (6), in which
the signal cable and the light guide are run through respective spaces that are different from each other and formed by the partitioning plate.

(8) The medical observation device according to any one of (1) to (7), in which
the signal cable includes a thin-line coaxial cable.

(9) The medical observation device according to any one of (1) to (7), in which
the first rotation axis unit supports a base end of the microscope unit.

(10) The medical observation device according to any one of (2) to (4) and (6) to (8), in which
the first rotation member is connected to a base end of the microscope unit.

(11) A medical observation system including:
a medical observation device including
a microscope unit that includes an image sensor and images an operative site, and
a holding unit that holds the microscope unit on a front end side; and
a display device that displays a picture imaged by the medical observation device, in which
in the medical observation device,
the holding unit includes a first rotation axis unit that supports the microscope unit to allow rotation about a first rotation axis substantially aligned with an optical axis of the microscope unit,
from the microscope unit, a cable group including at least a signal cable that transmits a signal related to the image sensor and a light guide that guides illuminating light for imaging is run towards an outside through an interior of a housing of the first rotation axis unit, and the cable group is run, at a position that does not match the first rotation axis when facing from the microscope unit towards the interior of the housing of the first rotation axis unit, in a direction substantially parallel to the first rotation axis, and run in a direction substantially parallel to a plane that is orthogonal to the first rotation axis in the interior of the housing of the first rotation axis unit.

What is claimed is:

1. A medical observation device comprising:
a microscope that includes an image sensor and images an operative site; and
a holder that holds the microscope on a front end side, wherein
the holder includes a first rotation axis support that supports the microscope to allow rotation about a first rotation axis substantially aligned with an optical axis of the microscope,
from the microscope, a cable group including at least a signal cable that transmits a signal related to the image sensor and a light guide that guides illuminating light for imaging is run towards an outside of the medical observation device through an interior of a housing of the first rotation axis support,
wherein
the first rotation axis support includes
a first rotation member that is connected to the microscope, and rotates together with the microscope about the first rotation axis, and
a second rotation member that supports the first rotation member to allow rotation about the first rotation axis on an opposite side from a side connected to the microscope, and
the cable group is run in the direction substantially parallel to a plane orthogonal to the first rotation axis inside the first rotation member.

2. The medical observation device according to claim 1, wherein
the first rotation member includes
a first member that is connected to the microscope and has a planar surface substantially orthogonal to the first rotation axis,
a second member that has a planar surface substantially orthogonal to the first rotation axis, and is disposed on an opposite side from a side of the first rotation member where the microscope is connected so that the planar surface has a predetermined interval with the planar surface of the first rotation member in a direction of the first rotation axis, and
a connecting member that connects the planar surface of the first member and the planar surface of the second member in the direction of the first rotation axis, and
the cable group is run in a direction substantially parallel to a plane orthogonal to the first rotation axis in a space between the planar surface of the first member and the planar surface of the second member.

3. The medical observation device according to claim 2, wherein
a cross-sectional area of the connecting member in the plane orthogonal to the first rotation axis is less than an area of a region on the planar surface of the first member, the region being enclosed by the cable group which curves when the microscope is rotated about the first rotation axis up to a limit of a movable range.

4. The medical observation device according to claim 1, wherein
the first rotation axis support includes
a first rotation member that is connected to the microscope, and rotates together with the microscope about the first rotation axis, and
a second rotation member that supports the microscope to allow rotation about the first rotation axis,
the first rotation member has a planar surface substantially orthogonal to the first rotation axis,
the second rotation member has a planar surface substantially orthogonal to the first rotation axis, and is disposed on an opposite side from a side of the first rotation member where the microscope is connected so that the planar surface has a predetermined interval with the planar surface of the first rotation member in a direction of the first rotation axis, and
the cable group is run in a direction substantially parallel to a plane orthogonal to the first rotation axis in a space between the planar surface of the first rotation member and the planar surface of the second rotation member.

5. The medical observation device according to claim 1, wherein
a partitioning plate is provided, the partitioning plate dividing a space in the interior of the housing of the first rotation axis support through which the cable group is run in the direction substantially parallel to the plane orthogonal to the first rotation axis into at least two spaces in a direction parallel to the first rotation axis.

6. The medical observation device according to claim 5, wherein
the signal cable and the light guide are run through respective spaces that are different from each other and formed by the partitioning plate.

7. The medical observation device according to claim 1, wherein
the signal cable includes a thin-line coaxial cable.

8. The medical observation device according to claim 1, wherein
the first rotation axis support supports a base end of the microscope.

9. The medical observation device according to claim 1, wherein
the first rotation member is connected to a base end of the microscope.

10. A medical observation system comprising:
a medical observation device including
a microscope that includes an image sensor and images an operative site, and
a holder that holds the microscope on a front end side; and
a display device that displays a picture imaged by the medical observation device, wherein
in the medical observation device,
the holder includes a first rotation axis support that supports the microscope to allow rotation about a first rotation axis substantially aligned with an optical axis of the microscope,
from the microscope, a cable group including at least a signal cable that transmits a signal related to the image sensor and a light guide that guides illuminating light for imaging is run towards an outside through an interior of a housing of the first rotation axis support, wherein
the first rotation axis support includes
- a first rotation member that is connected to the microscope, and rotates together with the microscope about the first rotation axis, and
- a second rotation member that supports the first rotation member to allow rotation about the first rotation axis on an opposite side from a side connected to the microscope, and the cable group is run in the direction substantially parallel to a plane orthogonal to the first rotation axis inside the first rotation member.

\* \* \* \* \*